(12) United States Patent
Kanno et al.

(10) Patent No.: US 11,957,313 B2
(45) Date of Patent: Apr. 16, 2024

(54) ENDOSCOPE, DISTAL END BARREL MEMBER OF ENDOSCOPE AND INSERTION PORTION OF ENDOSCOPE

(71) Applicant: OLYMPUS CORPORATION, Tokyo (JP)

(72) Inventors: Kenjiro Kanno, Komagane (JP); Shigeru Hosokai, Hachioji (JP); Takuro Horibe, Funabashi (JP); Daichi Kodama, Hachioji (JP); Hiroyuki Motohara, Hachioji (JP)

(73) Assignee: OLYMPUS CORPORATION, Tokyo (JP)

( * ) Notice: Subject to any disclaimer, the term of this patent is extended or adjusted under 35 U.S.C. 154(b) by 105 days.

(21) Appl. No.: 17/940,208

(22) Filed: Sep. 8, 2022

(65) Prior Publication Data

US 2023/0000316 A1    Jan. 5, 2023

Related U.S. Application Data

(63) Continuation of application No. PCT/JP2020/010344, filed on Mar. 10, 2020.

(51) Int. Cl.
*A61B 1/04*  (2006.01)
*A61B 1/00*  (2006.01)
(Continued)

(52) U.S. Cl.
CPC ............ *A61B 1/04* (2013.01); *A61B 1/00096* (2013.01); *A61B 1/05* (2013.01); *G02B 23/2423* (2013.01)

(58) Field of Classification Search
CPC .......... A61B 1/04; A61B 1/00096; A61B 1/05
See application file for complete search history.

(56) References Cited

U.S. PATENT DOCUMENTS

2009/0010140 A1*  1/2009  Ishii .................... A61B 1/05
2009/0058228 A1*  3/2009  Wakabayashi ........ B06B 1/0292
                                                      29/25.35
(Continued)

FOREIGN PATENT DOCUMENTS

EP   3 549 511 A1    10/2019
JP   H09-102657 A    4/1997
(Continued)

OTHER PUBLICATIONS

International Search Report dated Jun. 16, 2020 received in PCT/JP2020/010344.

*Primary Examiner* — Mishawn N. Hunter
(74) *Attorney, Agent, or Firm* — Scully, Scott, Murphy & Presser, P.C.

(57) ABSTRACT

An endoscope includes an imager unit loading region provided at a distal end portion of an insertion portion, a cable connection surface, a wall provided to connect an opening of the imager unit loading region and an opening of the cable connection surface to each other, a contact pattern formed on a wall surface of the imager unit loading region, a wiring pattern formed on a front surface of the cable connection surface from the wall, a connection pattern formed on the cable connection surface, and a through-electrode formed in the wall so that the imager unit loading region and the cable connection surface communicate with each other, configured to cause the contact pattern and the wiring pattern to electrically continue to each other, and formed at a predetermined angle with respect to a center axis of the distal end barrel member.

13 Claims, 27 Drawing Sheets

(51) Int. Cl.
*A61B 1/05* (2006.01)
*G02B 23/24* (2006.01)

(56) References Cited

U.S. PATENT DOCUMENTS

| | | | |
|---|---|---|---|
| 2014/0078287 A1* | 3/2014 | Ichihashi | A61B 1/00101 |
| | | | 348/82 |
| 2016/0183914 A1* | 6/2016 | Fujimura | A61B 8/4444 |
| | | | 600/459 |
| 2016/0370572 A1 | 12/2016 | Mikami | |
| 2017/0127915 A1 | 5/2017 | Viebach et al. | |
| 2017/0150873 A1* | 6/2017 | Tatebayashi | A61B 1/05 |
| 2017/0153441 A1 | 6/2017 | Ishizuka et al. | |
| 2017/0155860 A1 | 6/2017 | Ishizuka et al. | |
| 2017/0160537 A1* | 6/2017 | Ichihashi | A61B 1/00096 |
| 2018/0353060 A1* | 12/2018 | Miyahara | H04N 25/70 |
| 2019/0298153 A1 | 10/2019 | Sato et al. | |
| 2019/0343375 A1 | 11/2019 | Sato | |
| 2020/0000328 A1* | 1/2020 | Sakai | A61B 1/00013 |
| 2020/0178779 A1* | 6/2020 | Komoro | A61B 1/05 |
| 2023/0000325 A1* | 1/2023 | Motohara | A61B 1/0057 |
| 2023/0000327 A1* | 1/2023 | Motohara | A61B 1/00114 |

FOREIGN PATENT DOCUMENTS

| | | |
|---|---|---|
| JP | 2006-051259 A | 2/2006 |
| JP | 2008-131200 A | 6/2008 |
| JP | 2015-002788 A | 1/2015 |
| JP | 2017-505154 A | 2/2017 |
| JP | 2017-099530 A | 6/2017 |
| JP | 2017-108396 A | 6/2017 |
| JP | 2017-113417 A | 6/2017 |
| JP | 2017-209278 A | 11/2017 |
| JP | 2019-186619 A | 10/2019 |
| JP | 2019-195450 A | 11/2019 |
| WO | 2015/082328 A1 | 6/2015 |
| WO | 2015/133254 A1 | 9/2015 |
| WO | 2019/138462 A1 | 7/2019 |
| WO | 2020/044595 A1 | 3/2020 |
| WO | 2021/181526 A1 | 9/2021 |
| WO | 2021/181528 A1 | 9/2021 |

* cited by examiner

ENDOSCOPE, DISTAL END BARREL MEMBER OF ENDOSCOPE AND INSERTION PORTION OF ENDOSCOPE

CROSS REFERENCE TO RELATED APPLICATION

This application is a continuation application of PCT/JP2020/010344 filed on Mar. 10, 2020, the entire contents of which are incorporated herein by this reference.

BACKGROUND OF THE INVENTION

1. Field of the Invention

The present invention relates to an endoscope including a packaged electronic component in a distal end portion of an insertion portion, a distal end barrel member of the endoscope, and an insertion portion of the endoscope.

2. Description of the Related Art

Conventionally, in order to observe a site that is difficult to directly observe visually such as an inside part or the like of a living body or a structure, an endoscope has been widely used in a medical field or an industrial field. The endoscope is formed to be capable of being introduced toward an inside from an outside of the living body or the structure, and includes a configuration that can form an optical image or pick up the optical image.

In the endoscope as above, a distal end portion provided at a distal end of an insertion portion is mainly configured by a distal end unit in which various functional components are provided in a rigid distal end barrel. As the distal end barrel of the distal end unit like this, there has been proposed a distal end barrel using a technology of a molded interconnect device (MID) in recent years. For example, International Publication No. WO2015/082328 discloses an endoscope head as a distal end unit of an endoscope including a head body that is a distal end barrel including a MID device in which a plurality of conductive paths are formed, and various electronic components such as a camera module as an image pickup unit that is an imager unit supplied with electric power by the conductive paths.

Here, in the MID technology, it is possible to form a metal pattern only on a resin surface that can be irradiated with laser light or the like. A technology disclosed in International Publication No. WO2015/082328, which is a conventional art, adopts a configuration in which an opening portion is provided at one side of a camera accommodation space, and a conductive path as a wiring pattern that electrically connects to a camera module is formed on an outer peripheral surface of a distal end barrel continuing to the opening portion.

SUMMARY OF THE INVENTION

An endoscope in one aspect of the present invention includes: an insertion portion configured to be inserted into a subject; an imager unit comprising an objective optical system, and configured to convert an optical image from the objective optical system into an electric signal, and a distal end barrel member provided at a distal end portion of the insertion portion, formed of a resin material, and loaded with the imager unit, the distal end barrel member including, an imager unit loading region provided at a distal end side, with the imager unit being loaded on the imager unit loading region; a cable connection surface provided on a proximal end side; a wall provided to connect an opening of the imager unit loading region and an opening of the cable connection surface to each other; a contact pattern formed on a wall surface of the imager unit loading region and configured to be electrically connected to an electric contact of the imager unit; a wiring pattern formed on a front surface of the cable connection surface from the wall and configured to electrically continue to the contact pattern; a connection pattern formed on the cable connection surface and configured to electrically continue to the wiring pattern, with a core wire of a cable placed in the insertion portion being electrically connected to the connection pattern and a through-electrode formed on an inner surface of a through-hole that penetrates through the wall so that the imager unit loading region and the cable connection surface communicate with each other, configured to cause the contact pattern and the wiring pattern to electrically continue to each other, and formed at a predetermined angle with respect to a center axis of the distal end barrel member.

A distal end barrel member of an endoscope including an insertion portion configured to be inserted into a subject in one aspect of the present invention is provided at a distal end portion of the insertion portion, and includes: an imager unit loading region on which an imager unit configured to convert an optical image from an objective optical system into an electric signal is loaded; a cable connection surface provided on a proximal end side; a wall provided to connect an opening of the imager unit loading region and an opening of the cable connection surface to each other; a contact pattern formed on a wall surface of the imager unit loading region and configured to be electrically connected to an electric contact of the imager unit; a wiring pattern formed on a front surface of the cable connection surface from the wall and configured to electrically continue to the contact pattern; a connection pattern formed on the cable connection surface and configured to electrically continue to the wiring pattern, with a core wire of a cable placed in the insertion portion being electrically connected to the connection pattern; and a through-electrode formed on an inner surface of a through-hole that penetrates through the wall so as to connect the opening of the imager unit loading region and the opening of the cable connection surface to each other, configured to cause the contact pattern and the wiring pattern to electrically continue to each other, and formed at a predetermined angle with respect to a center axis of the distal end barrel member.

An insertion portion of an endoscope configured to be inserted into a subject in one aspect of the present invention is provided with a distal end barrel member at a distal end, and the distal end barrel member includes: an imager unit loading region on which an imager unit configured to convert an optical image from an objective optical system into an electric signal is loaded, a cable connection surface provided on a proximal end side; a wall provided to connect an opening of the imager unit loading region and an opening of the cable connection surface to each other; a contact pattern formed on a wall surface of the imager unit loading region and configured to be electrically connected to an electric contact of the imager unit; a wiring pattern formed on a front surface of the cable connection surface from the wall and configured to electrically continue to the contact pattern; a connection pattern formed on the cable connection surface, and configured to electrically continue to the wiring pattern, with a core wire of a cable placed in the insertion portion being electrically connected to the connection pattern; and a through-electrode formed on an inner surface of a through-hole that penetrates through the wall so as to connect the opening of the imager unit loading region and the opening of the cable connection surface to each other, configured to cause the contact pattern and the wiring pattern to electrically continue to each other, and formed at a predetermined angle with respect to a center axis of the distal end barrel member.

DETAILED DESCRIPTION OF THE PREFERRED EMBODIMENTS

Hereinafter, a distal end barrel member of an endoscope, a distal end unit and the endoscope of one aspect of the present invention are described based on the drawings. Note that in the following explanation, the drawings based on each of embodiments are schematic, attention should be paid to the fact that the relationship between the thickness and the width of each part, ratios of the thicknesses of respective parts and the like are different from the actual relationship and ratios, and there may be parts where the relationships and ratios of mutual dimensions are different among the drawings.

Further, as an endoscope in the following configuration explanation, there is illustrated a so-called flexible endoscope an insertion portion of which has flexibility to be inserted into a body cavity such as a bronchus, a urinary system, a stomach from an esophagus, a small intestine and a large intestine of a living body, but the present invention can also be applied to a so-called rigid endoscope with a rigid insertion portion that is used for surgery.

First Embodiment

An endoscope of one aspect according to a first embodiment of the present invention is described based on the drawings.

Figure 1:
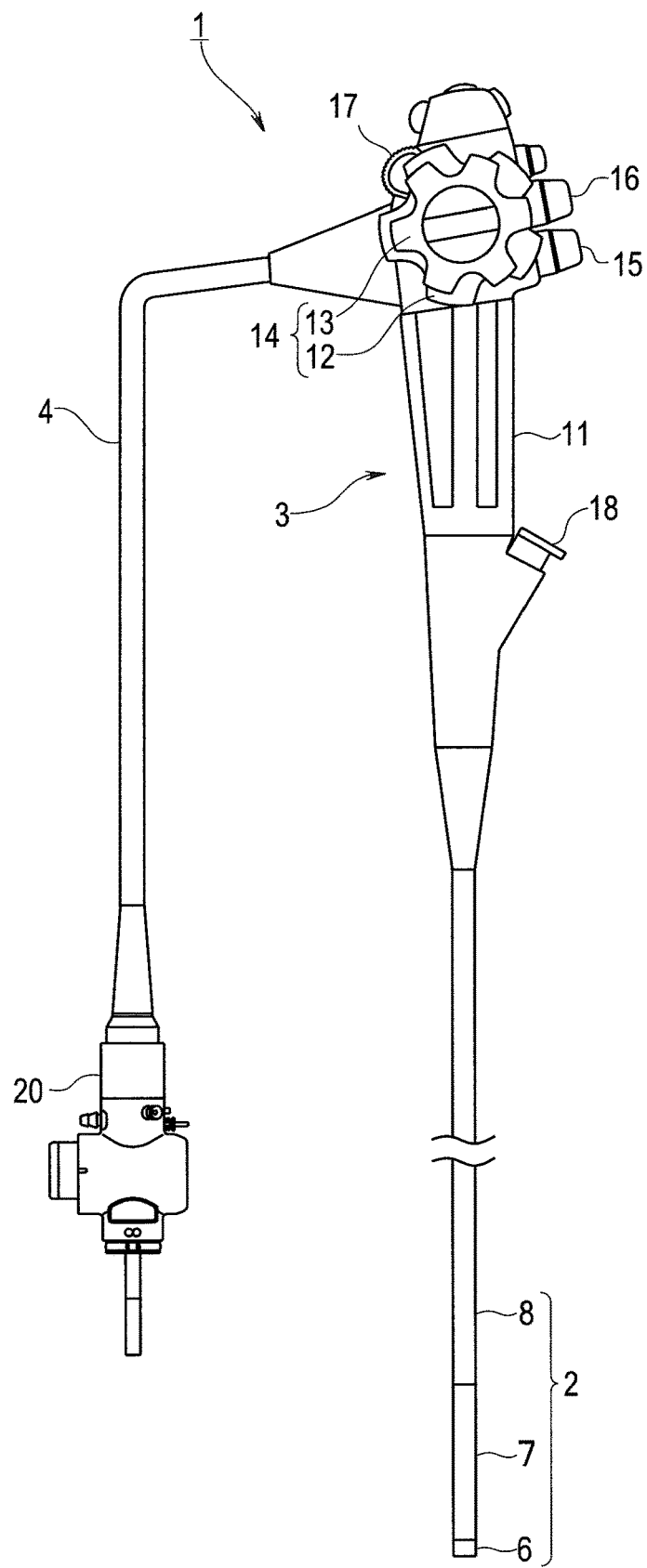
FIG. 1 is an external plan view of an endoscope according to a first embodiment of the present invention.

As shown in FIG. 1, an endoscope 1 of the present embodiment is configured by having a long elongated insertion portion 2 configured to be inserted into a subject, an operation portion 3, and a universal cable 4 that is a composite cable.

The insertion portion 2 of the endoscope 1 is configured by having a distal end portion 6, a bending portion 7, and a flexible tube portion 8 in order from a distal end.

On the operation portion 3, a bending operation knob 14 for operating to bend the bending portion 7 of the insertion portion 2 is turnably placed, and switches 15 and 16, a fixing lever 17 and the like are provided. The switches 15 and 16 switch various endoscope functions, and observation images such as near point observation, far point observation, release, and still images. The fixing lever 17 fixes turning of the bending operation knob 14.

Note that in the bending operation knob 14, two rotation knobs each in a substantially disk shape that are a UD bending operation knob 12 for operating to bend the bending portion 7 in an up-down direction, and an RL bending operation knob 13 for operating to bend the bending portion 7 in a left-right direction are placed to be superimposed on each other.

A connection portion of the insertion portion 2 and the operation portion 3 is configured by having a grasping portion 11 grasped by a user, and a treatment instrument insertion channel insertion portion 18 that is disposed in the grasping portion 11 to be an opening portion of a treatment instrument insertion channel that allows insertion of various treatment instruments and is placed in the insertion portion 2.

The universal cable 4 provided to extend from the operation portion 3 has an endoscope connector 20 attachable to and detachable from a light source apparatus not illustrated, at an extension end. Note that the endoscope 1 of the present embodiment transmits illumination light from the light source apparatus (not illustrated) to the distal end portion 6 by a light guide bundle (not illustrated) of illumination means inserted through and placed in the insertion portion 2, the operation portion 3 and the universal cable 4.

To the endoscope connector 20, a coil-shaped electric cable is connected though not illustrated here, and an electric connector attachable to and detachable from a video processor (not illustrated) is provided at an extension end of the electric cable.

Here, a configuration of a distal end portion of the insertion portion 2 of the endoscope 1 of the present embodiment will be described hereinafter based on FIG. 2 and FIG. 3. Note that in the following explanation, concerning a well-known configuration of the insertion portion 2, explanation is simplified or omitted.

Figure 2:
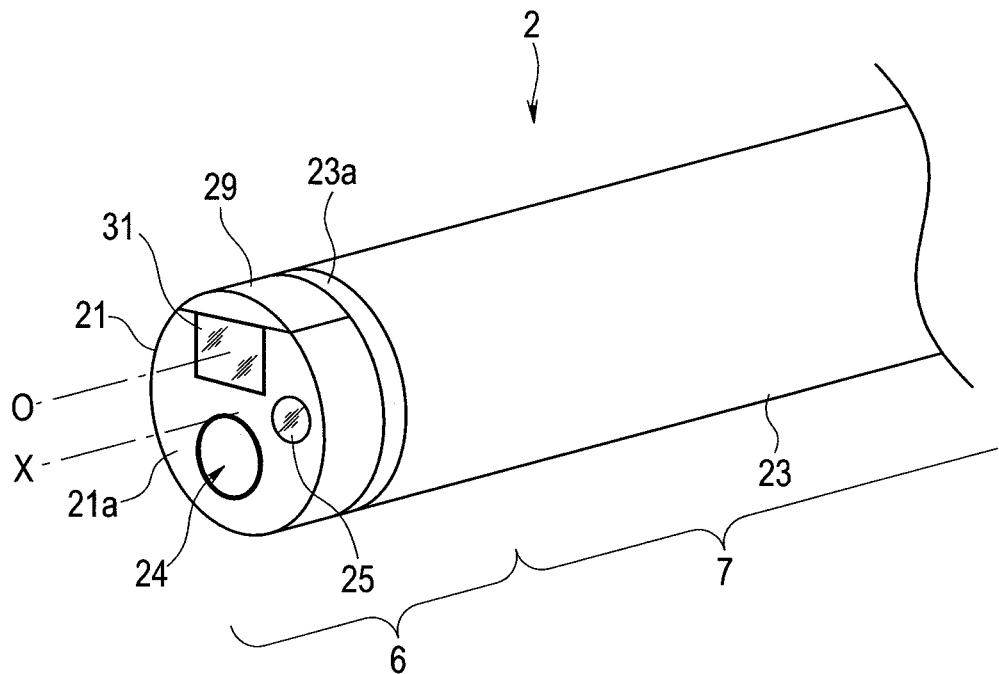
FIG. 2 is a partial cross-sectional view showing a configuration of a distal end portion of an insertion portion according to the first embodiment of the present invention.
Figure 3:
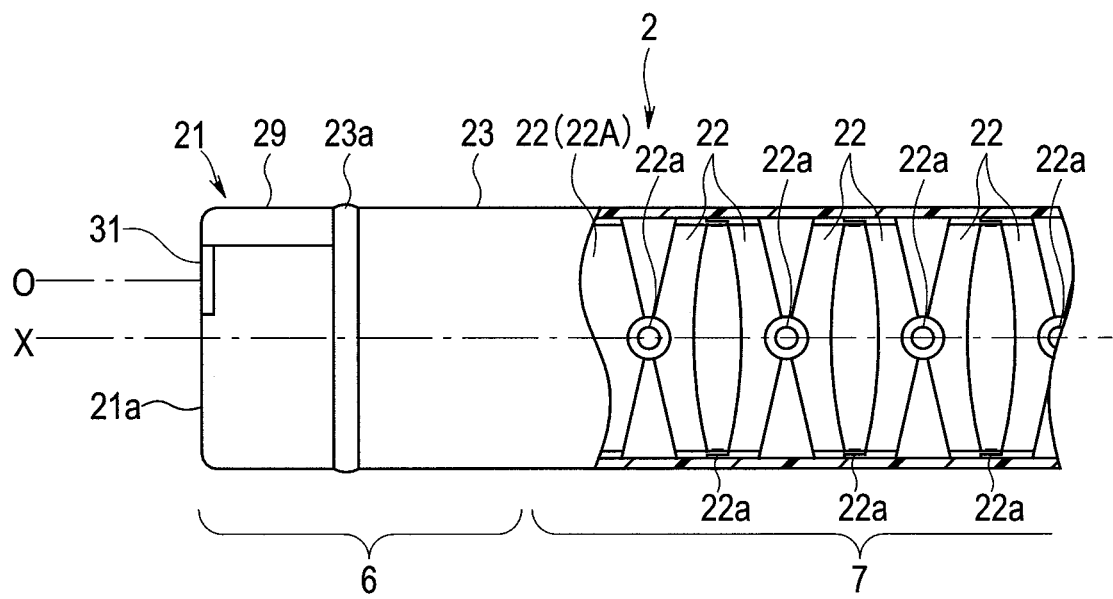
FIG. 3 is a perspective view showing a configuration of the distal end portion of the insertion portion according to the first embodiment of the present invention.

As shown in FIG. 2 and FIG. 3, the distal end portion 6 of the insertion portion 2 is provided with an observation window 31, an illumination window 25, and a channel opening portion 24, on a distal end surface 21a, and includes a distal end barrel member 21 as a distal barrel (also referred to as a distal end configuration portion or a distal end rigid portion) that is a barrel component formed of a nonconductive resin material in a substantially circular columnar block body having insulation properties.

In the distal end barrel member 21, a distal end portion is substantially circular in cross-sectional shape orthogonal to a center axis X. The distal end barrel member 21 is covered with a tube-shaped bending rubber 23 from a middle toward a proximal end side, and a distal end of the bending rubber 23 is fixedly attached by a bobbin winding bonded portion 23a. Note that the bending rubber 23 integrally covers a plurality of bending pieces 22 (22A) that are bending tubes provided in the bending portion 7. The plurality of bending pieces 22 (22A) are provided to be turnably connected to each other by pivotable support portions 22a such as rivets.

Figure 4:
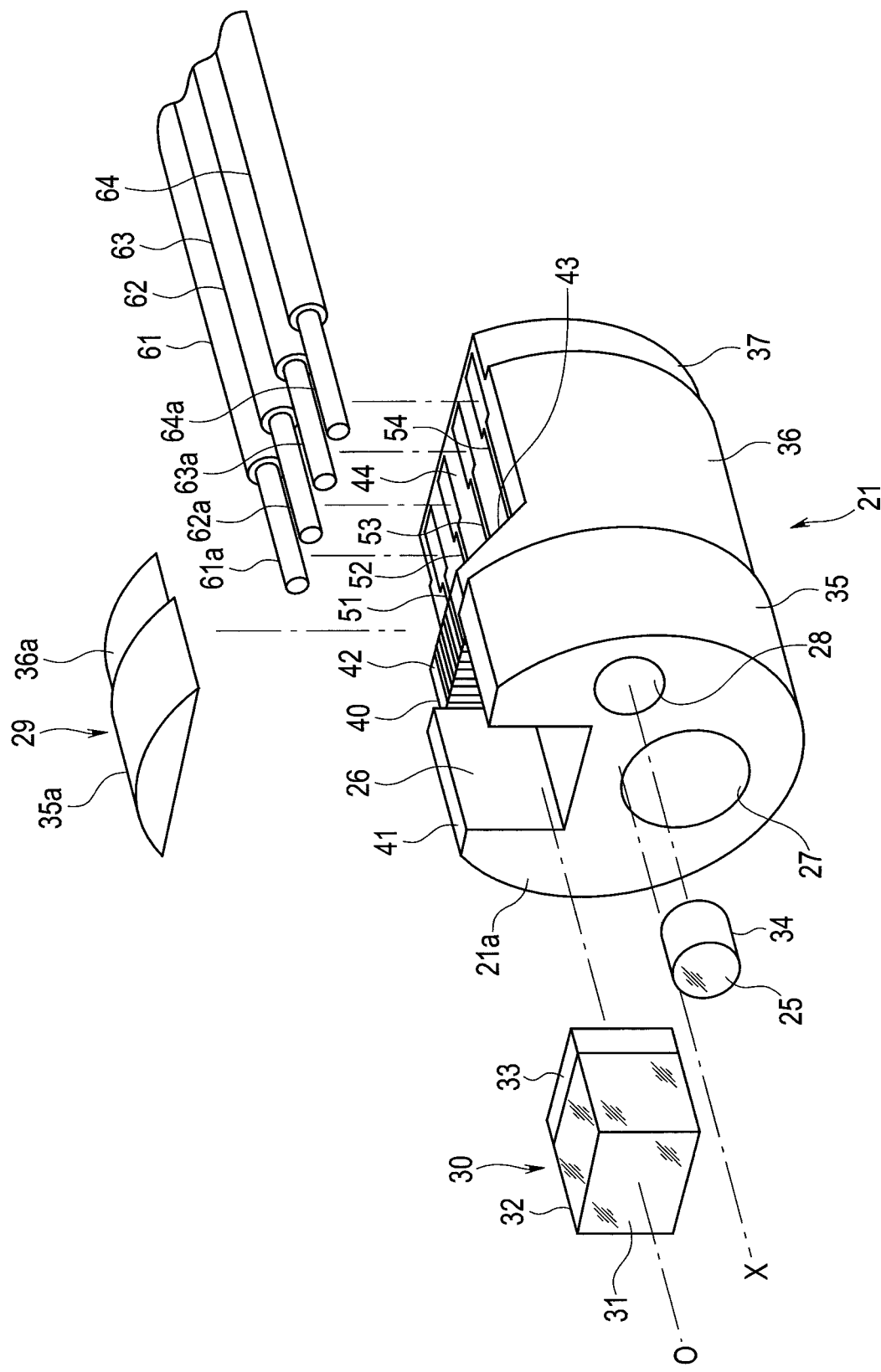
FIG. 4 is an exploded perspective view showing a configuration of a distal end barrel member according to the first embodiment of the present invention.

In the distal end portion 6 of the present embodiment, the rigid distal end barrel member 21 including a molded interconnect device (MID) and forming a substantially circular columnar shape is provided. As shown in FIG. 4, in the distal end barrel member 21, various functional components such as a camera module 30 as an image pickup unit are provided.

Here, the camera module 30 provided in the distal end barrel member 21 as one of the functional components in the present embodiment is configured by a CSP (chip size package) in which a lens unit for image pickup that is formed of a lens stacked body produced by using a wafer level optics technology, a cover glass, and a lens unit 32 bonded to the cover glass via a bonding layer and an image pickup device 33 are integrally stacked and packaged, for example.

In the camera module 30 as above, the lens unit 32 is manufactured, for example, by producing a plurality of lens wafers in each of which a lens is formed on a base material such as a glass substrate, and stacking and dicing the lens wafers, and the like.

Accordingly, the lens unit 32 of the present embodiment is a lens unit that forms a rectangular shape in plan view shape, and does not have a lens barrel. The image pickup device 33 also has a plan view shape formed into a rectangular shape by dicing or the like, and the camera module 30 of the present embodiment has an extremely small entire body with a lens surface of, for example, approximately 1 mm square forming a substantially rectangular parallelepiped shape.

Figure 5:
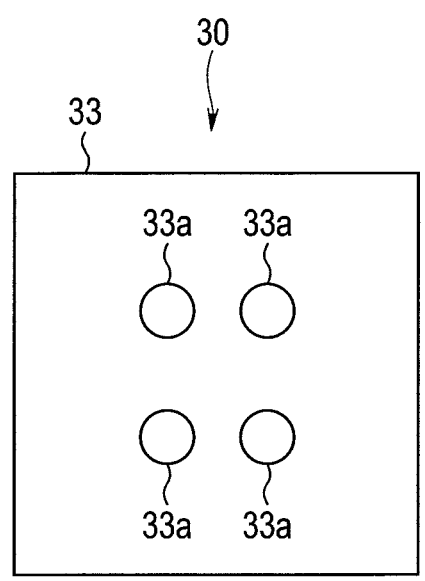
FIG. 5 is a plan view showing a configuration of a back surface of a camera module according to the first embodiment of the present invention.

Note that in the camera module 30, a plurality of, here four, terminals 33a that are electric contacts are provided on a back surface of the image pickup device 33, as shown in FIG. 5.

The distal end barrel member 21 is formed into a substantially columnar shape (in the present embodiment, more specifically, a substantially circular columnar shape) by injection molding using a resin material, for example. The distal end barrel member 21 has a large diameter portion 35 on a distal end side. From the large diameter portion 35 to a proximal end side, a first small diameter portion 36 that has a step portion in an inside diameter direction and is covered with the bending rubber 23 is formed. From the first small diameter portion 36 to the proximal end side, a second small diameter portion 37 that has a step portion further in the inside diameter direction, and serves as a fitting portion on which a distal end portion of the bending piece 22A at a distalmost end is fitted is formed.

In the distal end barrel member 21, a diameter of the large diameter portion 35 is, for example, about 2 mm to 5 mm and very small, and the distal end surface 21a to be a surface on the distal end side of the distal end portion 6, and a part on a distal end side from the bobbin winding bonded portion 23a on an outer peripheral surface of the large diameter portion 35 form an outer peripheral shape of the distal end portion 6. Accordingly, as a resin material configuring the distal end barrel member 21, a material that is not only compatible with the MID technology but also has biocompatibility is selected. Note that a diameter of the insertion portion 2 of the present embodiment is also a thin diameter of about 2 mm to 5 mm, for example.

Here, in the present embodiment, the distal end barrel member 21 refers to a resin portion formed by injection molding, for example, and has various wiring patterns and the like (described later) of metal patterns using the MID technology that forms circuits by plating a part activated by irradiating laser light on a surface of the distal end barrel member 21.

In the large diameter portion 35 of the distal end barrel member 21, a module accommodation chamber 26, an illumination component accommodation chamber 28, and a channel holding chamber 27 are formed. The module accommodation chamber 26 is an imager unit loading region in a rectangular recessed portion shape as an accommodation chamber configured to accommodate the camera module 30 that is an optical functional component. The illumination component accommodation chamber 28 is an accommodation chamber configured to accommodate, from a proximal end side, a distal end portion of a light guide bundle 72 (see FIG. 10) that is an optical functional component, and has the illumination lens 34 to be the illumination window 25 fitted to a distal end side. The channel holding chamber 27 is configured to allow insertion of a distal end portion of a treatment instrument channel 71 (see FIG. 9) and hold the distal end portion of the treatment instrument channel 71.

Note that the channel holding chamber 27 and the illumination component accommodation chamber 28 are through-holes circular in cross-section that penetrate through a proximal end surface 21b from a distal end surface 21a of the distal end barrel member 21.

Figure 6:
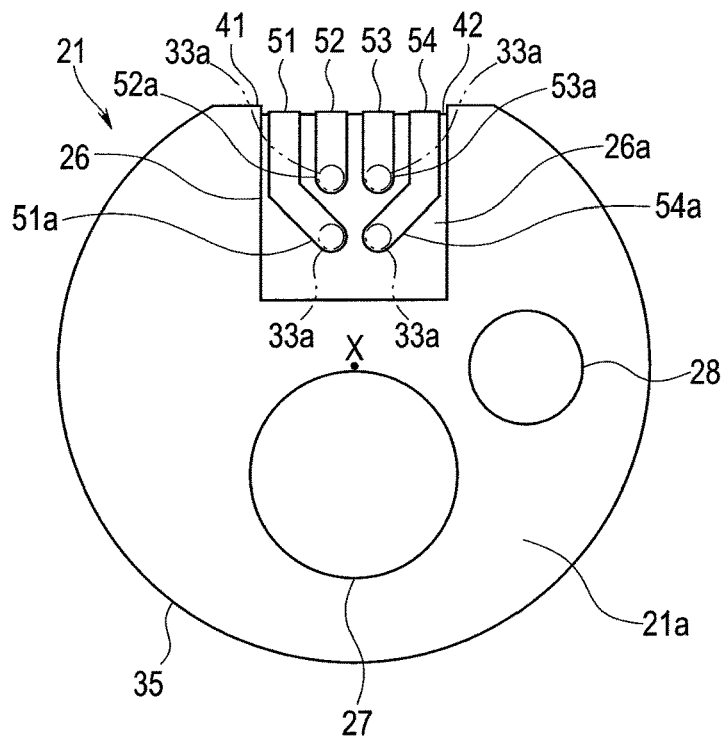
FIG. 6 is a front view showing the configuration of the distal end barrel member according to the first embodiment of the present invention.

The module accommodation chamber 26 has a distal end opening portion in the distal end surface 21a of the distal end barrel member 21, and a mounting surface 26a that is a planar wall surface orthogonal to the center axis X in a depth direction in a center axis X (insertion axis) direction as shown in FIG. 6, with a side portion in one direction (upward as seen toward a paper surface) that is orthogonal to the center axis X being opened, and is a rectangular recessed portion in a substantially similar shape to an outer shape of the camera module 30. Note that the center axis X of the distal end barrel member 21 corresponds to a longitudinal center axis of the insertion portion 2 in a straight line state.

On the mounting surface 26a of the module accommodation chamber 26, four contact patterns 51a to 54a are formed. The four contact patterns 51a to 54a are wiring patterns to which the terminals 33a (here, four) that are electric contacts provided on the back surface of the image pickup device 33 of the camera module 30 are electrically connected. Among the four contact patterns 51a to 54a, contact patterns 51a and 54a on both sides are formed so that middle portions bend inward to correspond to positions of the terminals 33a of the camera module 30. The four contact patterns 51a to 54a are also formed by using the MID technology.

To the distal end barrel member 21, a lid body 29 (see FIG. 4) that closes the opening on the side portion side is fixedly attached by bonding or the like in a state in which the camera module 30 is accommodated in the module accommodation chamber 26. Note that the camera module 30 is mounted in the module accommodation chamber 26 so that an optical axis O of photographing light becomes parallel to the center axis X.

The distal end barrel member 21 may have a configuration in which the opening on the side portion side is filled with a resin material such as an underfill material in a range similar to a region covered with the lid 29, or a range covering the camera module 30 and the wirings 51 to 54 described later, instead of being covered with the lid 29.

The lid body 29 is formed into a half-moon shape in cross-section in which arc surfaces 35a and 36a having a level difference are formed so that outer peripheries correspond to the large diameter portion 35 and the small diameter portion 36 in a state in which the lid body 29 is fitted to the distal end barrel member 21. Note that a bonding surface 41 to be bonded to a bottom surface of the lid body 29 is formed on the large diameter portion 35 of the distal end barrel member 21.

Figure 7:
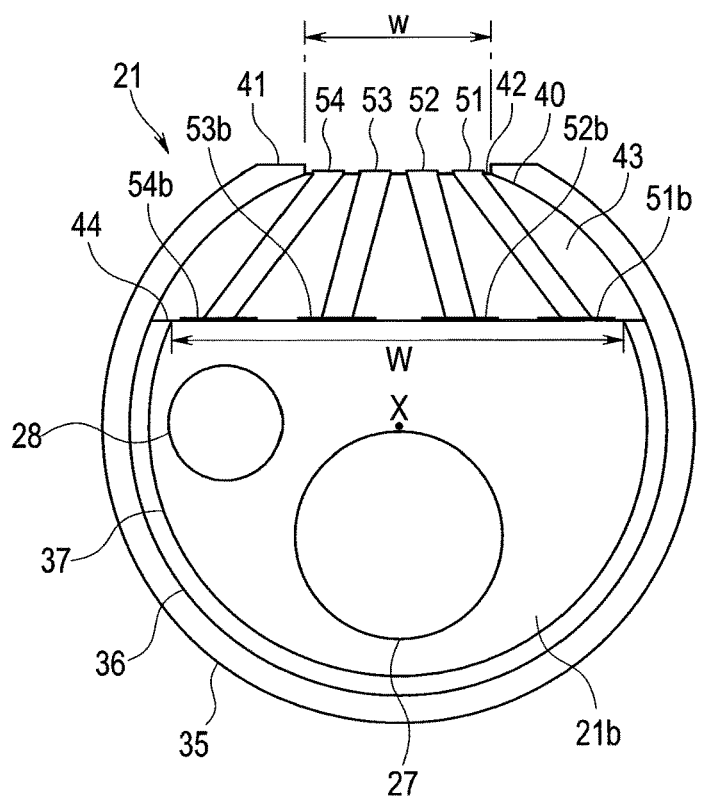
FIG. 7 is a back view showing the configuration of the distal end barrel member according to the first embodiment of the present invention.
Figure 8:
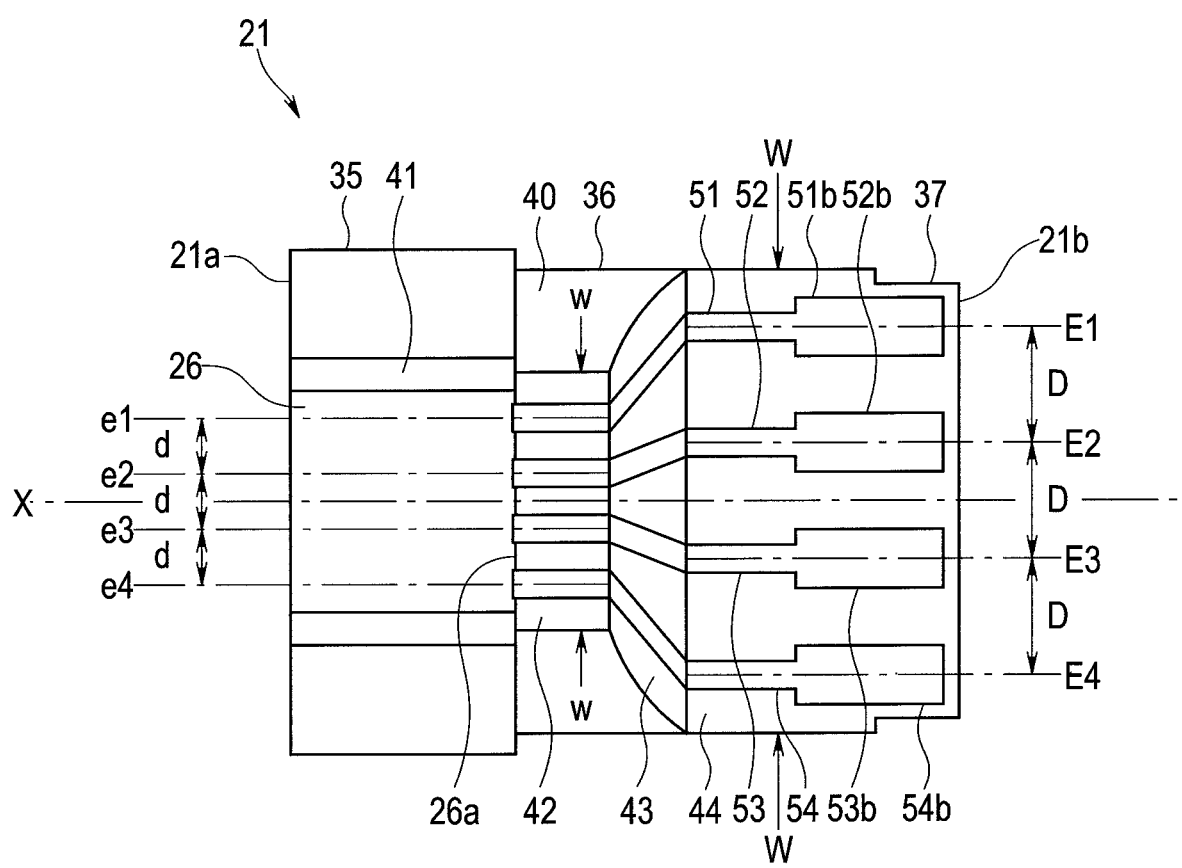
FIG. 8 is a top view showing the configuration of the distal end barrel member according to the first embodiment of the present invention.

As shown in FIG. 7 and FIG. 8, the distal end barrel member 21 has a first wiring formation surface 42 in the large diameter portion 35, a second wiring formation surface 43 in the first small diameter portion 36, and a third wiring formation surface 44 from a middle of the first small diameter portion 36 to the second small diameter portion 37. The first wiring formation surface 42 is a flat surface parallel to the center axis X with a slight level difference in an inside diameter direction (center axis X direction) from the bonding surface 41. The second wiring formation surface 43 is an inclined surface inclining at a predetermined angle in the inside diameter direction toward a proximal end side from the first wiring formation surface 42. The third wiring formation surface 44 is a flat surface parallel to the center axis X toward the proximal end side from the second wiring formation surface 43.

In other words, in the distal end barrel member 21, the two flat surfaces (the first and the third wiring formation surfaces 42 and 44) extending in the center axis X direction and located at different horizontal positions are formed, and the inclined surface (the second wiring formation surface) connecting the two flat surfaces is formed. Accordingly, in the distal end barrel member 21, a wall portion 40 is formed between the mounting surface 26a of the module accommodation chamber 26 and the second wiring formation surface 43.

Note that the second wiring formation surface 43 that is the inclined surface to be a proximal end surface of the wall portion 40 inclines in a direction of the proximal end side toward a distal end side of the third wiring formation surface 44 from a proximal end side of the first wiring formation surface 42.

On the third wiring formation surface 44 at the proximal end side, a cable connection surface is configured. On the cable connection surface, four rectangular lands 51b to 54b as cable connection electrodes to which respective core wires 61a to 64a of four cables 61 to 64 for power supply and for signals are connected are provided in parallel with predetermined separation distances in a direction orthogonal to the center axis X.

On the first to the third wiring formation surfaces 42 to 44, four wiring patterns 51 to 54 are formed. The four wiring patterns 51 to 54 are conductive paths that allow four contact patterns 51a to 54a formed on the mounting surface 26a to electrically continue to the four lands 51b to 54b formed on the third wiring formation surface 44. In other words, the four wiring patterns 51 to 54 are formed to extend over the third wiring formation surface 43 from the first wiring formation surface 42.

Here, in the four wiring patterns 51 to 54 formed on the first wiring formation surface 42, mutual separation distances d of longitudinal center axes e1 to e4 adjacent to one another are set to be short (small) according to the four terminals 33a that are the electrodes of the small camera module 30 of 1 mm square, for example. Note that in the four wiring patterns 51 to 54 of the first wiring formation surface 42, the mutual separation distances d are formed to be the same distance as a width of the terminal 33a of the camera module 30, for example.

In the four wiring patterns 51 to 54 formed on the third wiring formation surface 44, separation distances D of longitudinal center axes E1 to E4 adjacent to one another are set to be longer (larger) than the separation distances d of the four wiring patterns 51 to 54 on the first wiring formation surface 42, in consideration of workability of connecting the respective core wires 61a to 64a of the four cables 61 to 64 to the four lands 51b to 54b by soldering or the like.

Accordingly, on the second wiring formation surface 43 that is the inclined surface connecting the first wiring formation surface 42 and the third wiring formation surface 44, the four wiring patterns 51 to 54 that extend radially in the center axis X direction that is the inside diameter direction are formed.

In other words, as shown in FIG. 7 and FIG. 8, in the distal end barrel member 21, a width W of the third wiring formation surface 44 is set to be longer (larger) than a width w of the first wiring formation surface 42 in the direction orthogonal to the center axis X (W>w). Note that the width w of the first wiring formation surface 42 is the same as a width of the mounting surface 26a here. In other words, the width W of the third wiring formation surface 44 is wider (larger) than a width of the camera module 30.

The third wiring formation surface 44 also has a length in the direction along the center axis X set to be longer than the first wiring formation surface 42 and has a larger surface area than the first wiring formation surface 42.

Accordingly, surface areas of the four lands 51b to 54b formed on the third wiring formation surface 44 can also be made large, so that workability of connection of the respective core wires 61a to 64a of the four cables 61 to 64 is also enhanced.

In the distal end barrel member 21 configured as above, the camera module 30 is mounted, the illumination lens 34, the light guide bundle 72 and the treatment instrument channel 71 are assembled, and the respective core wires 61a to 64a of the four cables 61 to 64 are connected to the corresponding four lands 51b to 54b on the third wiring formation surface 44 by soldering or the like.

Note that when the camera module 30 is mounted in the distal end barrel member 21, the four terminals 33a of the image pickup device 33 are electrically connected to the corresponding four contact patterns 51a to 54a on the mounting surface 26a by reflow-soldering.

Figure 9:
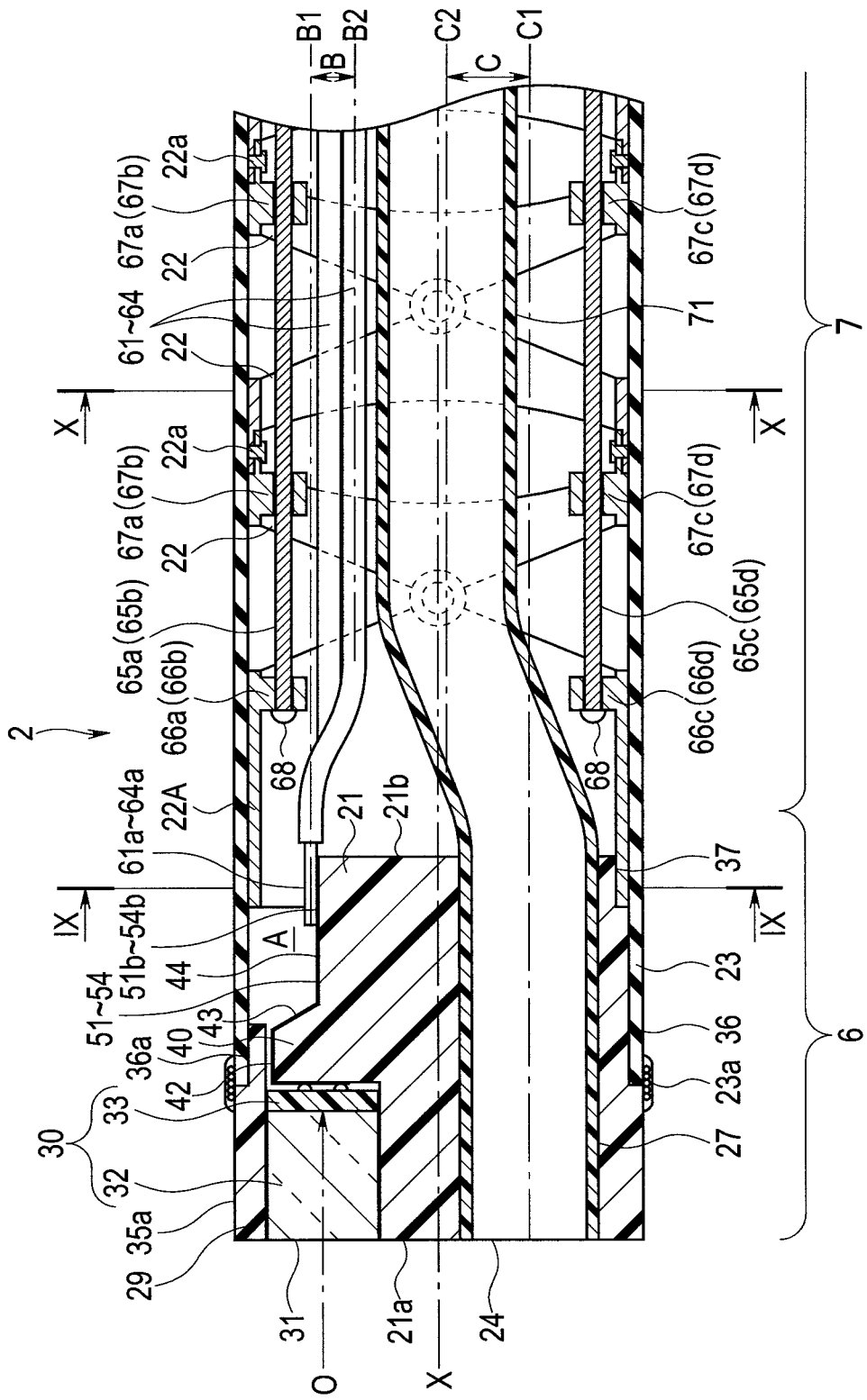
FIG. 9 is a cross-sectional view showing the configuration of the distal end portion of the insertion portion according to the first embodiment of the present invention.

The distal end barrel member 21 is assembled to the distal end portion 6 of the insertion portion 2 as shown in FIG. 9. In the distal end portion of the insertion portion 2, four cables 61 to 64 provided to extend from the distal end barrel member 21 to a proximal end side in the insertion portion 2 are bent at a predetermined angle to a center axis X side that is the inside diameter direction in the bending piece 22A at a distalmost end. Thereafter, the four cables 61 to 64 are bundled and provided to be inserted along the center axis X side in the insertion portion 2 at the proximal end side from the distal end portion of the bending portion 7.

For example, one of the cables 61 to 64 is disposed so that a center axis B2 of a portion provided to extend to the proximal end side from the bending portion 7 is deviated in the inside diameter direction by a predetermined distance B with respect to a center axis B1 of a distal end connected to the distal end barrel member 21. In other words, the center axis B2 is disposed closer to the center axis X by the distance B than the center axis B1.

In a treatment instrument channel 71, a proximal end portion is also bent at a predetermined angle to the center axis X side that is the inside diameter direction from the distal end barrel member 21, and is provided to be inserted along the center axis X side in the insertion portion 2 at the proximal end side from the distal end portion of the bending portion 7.

In other words, the treatment instrument channel 71 is disposed so that a center axis C2 of a portion provided to extend to the proximal end side from the bending portion 7 is deviated by a predetermined distance C in the inside diameter direction with respect to a center axis C1 of a distal end portion fitted to the distal end barrel member 21. In other words, the center axis C2 is disposed closer to the center axis X by the distance C than the center axis C1. The center axes C1 and C2 that are axes of the treatment instrument channel 71 are both substantially parallel to the center axis X that is the axis of the distal end barrel member 21 except for a bent portion.

In this way, in the four cables 61 to 64 and the treatment instrument channel 71, positions at which the four cables 61 to 64 and the treatment instrument channel 71 are inserted to the proximal end side from the distal end portion of the bending portion 7 are deviated (disposed to be close to the center axis X) in the inside diameter direction from positions at which the four cables 61 to 64 and the treatment instrument channel 71 are connected to the distal end barrel member 21. In this way, the four cables 61 to 64 and the treatment instrument channel 71 are inserted at positions that do not interfere with four bending operation wires 65a to 65d that operate to turn the plurality of bending pieces 22 (22A) in the insertion portion 2.

Note that the four bending operation wires 65a to 65d are provided in a proximal end inner peripheral portion of the bending piece 22A at the distalmost end, and are connected to four wire fixing portions 66a to 66d that protrude in the inside diameter direction by brazing 68 or the like. The four bending operation wires 65a to 65d are inserted through and held in a plurality of wire guides 67a to 67d provided to protrude in the inside diameter direction from inner peripheral portions of a plurality of bending pieces 22 to be able to advance and retreat.

The four cables 61 to 64 and the treatment instrument channel 71 are disposed so as not to interfere with the four wire fixing portions 66a to 66d and the plurality of wire guides 67a to 67d that protrude in the inside diameter direction, in the bending portion 7.

In other words, the four cables 61 to 64 and the treatment instrument channel 71 are placed by being bent so that shapes to a distal end side further from distal ends of the four wire fixing portions 66a to 66d that fix distal ends of the respective bending operation wires 65a to 65d that operate to bend the bending portion 7 separate in an outer periphery direction (outside diameter direction) from the center axis X of the distal end barrel member 21.

Figure 10:
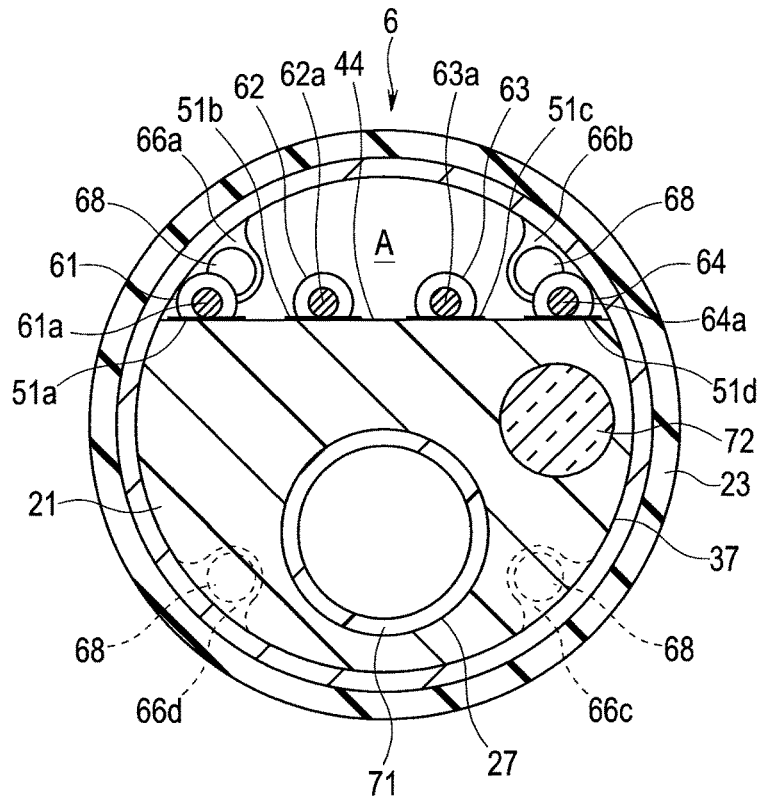
FIG. 10 is an essential part cross-sectional view of the distal end portion of the insertion portion along line IX-IX in FIG. 8 according to the first embodiment of the present invention.
Figure 11:
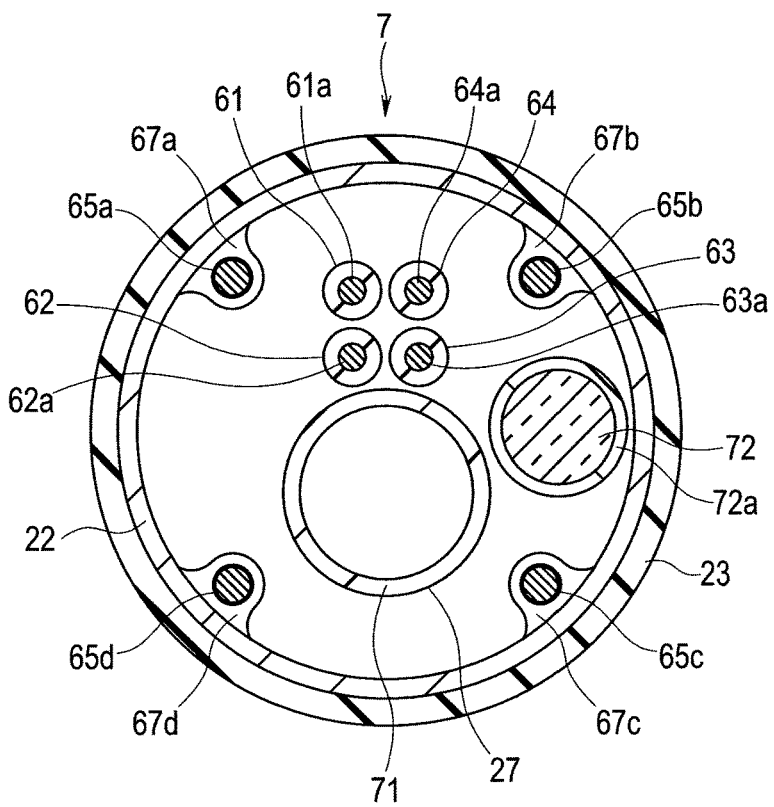
FIG. 11 is an essential part cross-sectional view of a bending portion of the insertion portion along line X-X in FIG. 8 according to the first embodiment of the present invention.

The four wire fixing portions 66a to 66d and the four wire guides 67a to 67d here are provided at substantially equal intervals at positions where an up, a down, a left and a right of the bending portion 7 are rotated 90° around the center axis X, as shown in FIG. 10 and FIG. 11. In other words, the four wire guides 67a to 67d are provided at positions rotated 45° with respect to a line perpendicular to the center axis X and the third wiring formation surface 44 (flat surface), or a line perpendicular to the center axis X and parallel to the third wiring formation surface 44 (flat surface).

For example, when the bending portion 7 is bent upward, the two bending operation wires 65a and 65b on an upper side are towed, and the two bending operation wires 65c and 65d on a lower side are relaxed. When the bending portion 7 is bent downward, the two bending operation wires 65a and 65b on the upper side are relaxed, and the two bending operation wires 65c and 65d on the lower side are towed.

When the bending portion 7 is bent leftward, the two bending operation wires 65b and 65d are towed, and the two bending operation wires 65a and 65c are relaxed. When the bending portion 7 is bent rightward, the two bending operation wires 65b and 65d are relaxed, and the two bending operation wires 65a and 65c are towed.

The bending portion 7 becomes bendable in all directions around the center axis X by towing and relaxing operations combining the four bending operation wires 65a to 65d variously. Note that as shown in FIG. 11, the light guide bundle 72 is covered with an outer sheath 72a in the insertion portion 2.

The endoscope 1 of the present embodiment configured as above has a configuration in which the four contact patterns 51a to 54a to which the terminals 33a of the camera module 30 are electrically connected, and the wiring patterns 51 to 54 that are conductive paths that allow the four contact patterns 51a to 54a to electrically continue to the four lands 51b to 54b of the third wiring formation surface 44 as the cable connection surface are formed on the first wiring formation surface 42 that is a flat surface and the second wiring formation surface 43 that is an inclined surface, by using the MID technology in the distal end barrel member 21 that is placed at the distal end portion 6 of the insertion portion 2.

The distal end barrel member 21 is formed so that the third wiring formation surface 44 on which the four lands 51b to 54b are formed has the level difference at the center axis X side in the inside diameter direction with respect to the first wiring formation surface 42. Accordingly, the distal end barrel member 21 can secure a space in which the four cables 61 to 64 are disposed laterally side by side and connected, above the third wiring formation surface 44. In other words, in the distal end portion 6, a space A can be formed above the third wiring formation surface 44 of the distal end barrel member 21, and the four cables 61 to 64 are configured to be connected in the space A.

Accordingly, the distal end barrel member 21 does not need to expand in the outside diameter direction to secure the space to connect the four cables 61 to 64, and increase in diameter of the distal end barrel member 21 is restrained. In other words, a proximal end portion (in particular, a distal end side of the wire fixing portions 66a to 66d) of the distal end barrel member 21 often becomes a dead space, and by effectively using the dead space like this by forming a step portion, it becomes possible to secure the space (space A) in which the four cables 61 to 64 can be connected in the distal end portion 6 without increasing the diameter of the distal end barrel member 21. As a result, in the endoscope 1, increase in the diameter of the distal end portion 6 is also restrained, and it becomes possible to reduce the diameter of the insertion portion 2.

The space A to connect the four cables 61 to 64 is formed at the distal end side from the four wire fixing portions 66a to 66d that fix the distal end portions of the four bending operation wires 65a to 65d.

Accordingly, the space A is superimposed with the four wire fixing portions 66a to 66d in a projection along the center axis X, but is at the position deviated in a front-back direction along the center axis X, so that connection portions of the four lands 51b to 54b on the third wiring formation surface 44 and the respective core wires 61a to 64a of the four cables 61 to 64 can be prevented from interfering with the four wire fixing portions 66a to 66d.

Since the third wiring formation surface 44 is wider (larger) than the width of the camera module 30, a region in which the four lands 51b to 54b are formed can be taken widely. Accordingly, the surface areas and the pitches (intervals) of the four lands 51b to 54b can be taken to be large.

Thereby, in the endoscope 1, the connection work by soldering or the like of the respective core wires 61a to 64a of the four cables 61 to 64 becomes easy, even when the camera module 30 that is an electronic component loaded in the distal end portion 6 of the insertion portion 2 is a very small image pickup unit of a CSP (chip size package) in which the lens unit 32 and the image pickup device 33 are integrally stacked and packaged.

From the above explanation, in the endoscope 1 of the present embodiment, it is possible to enhance workability of connection of the plurality of cables 61 to 64 in the distal end barrel member 21 that is provided at the distal end portion 6 of the insertion portion 2.

First Modification

Figure 12:
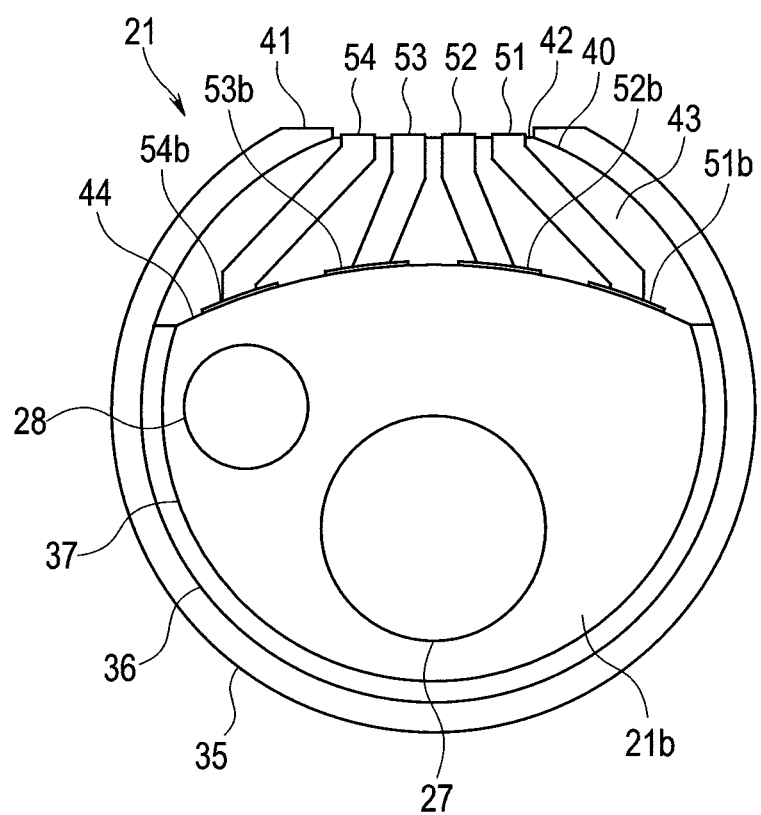
FIG. 12 is a back view showing a configuration of a distal end barrel member according to a first modification of the first embodiment of the present invention.

As shown in FIG. 12, by making a third wiring formation surface 44 of a distal end barrel member 21 a circular arc surface instead of a flat surface, it is possible to take larger pitches (intervals) among the four lands 51b to 54b.

Second Modification

Figure 13:
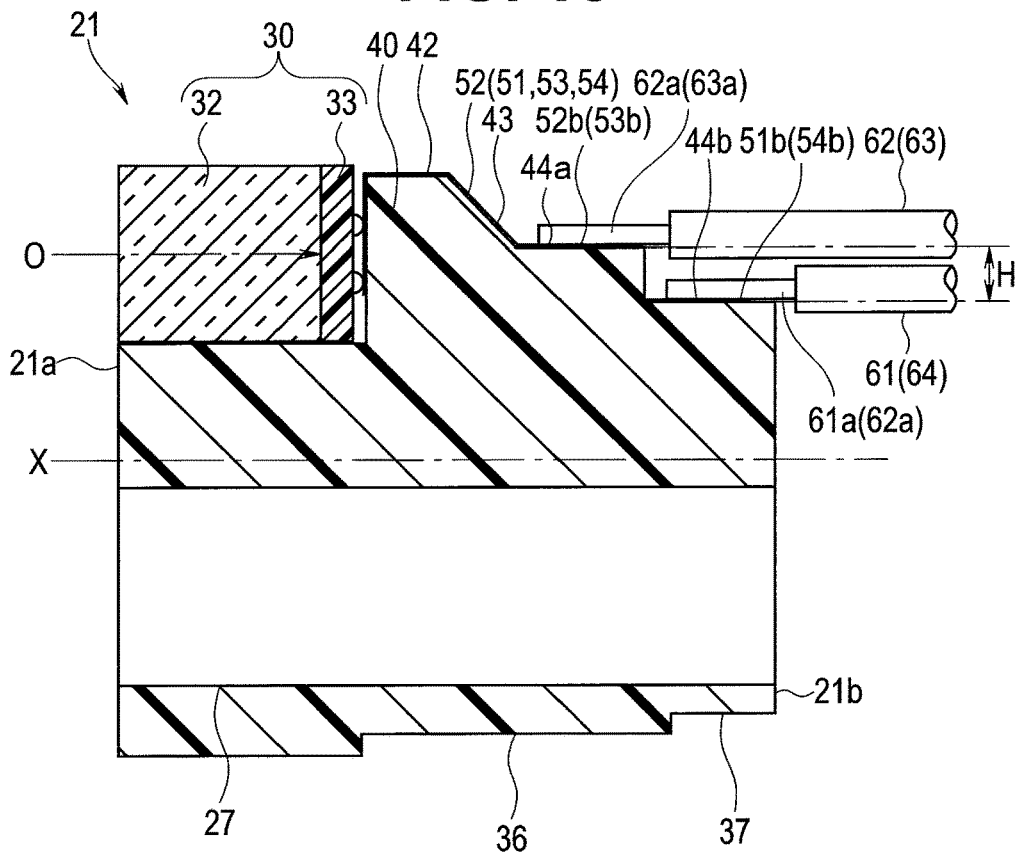
FIG. 13 is a cross-sectional view showing a configuration of a distal end barrel member according to a second modification of the first embodiment of the present invention.
Figure 14:
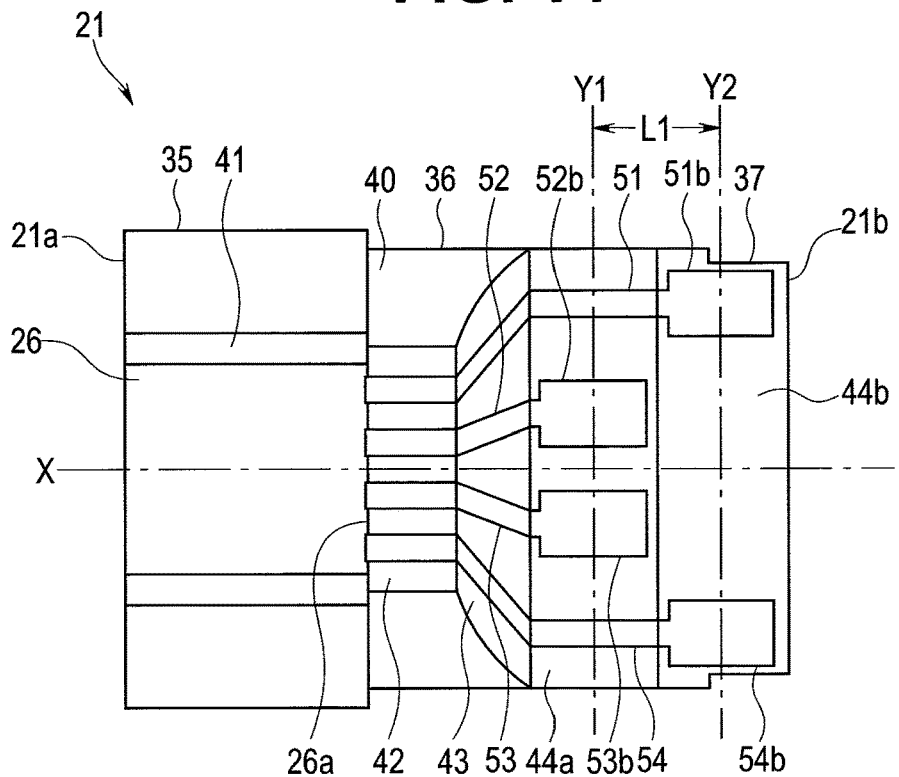
FIG. 14 is a top view showing the configuration of the distal end barrel member according to the second modification of the first embodiment of the present invention.

As shown in FIG. 13 and FIG. 14, the distal end barrel member 21 may be configured to have a third wiring formation surface 44a on a proximal end side from a second wiring formation surface 43, and a fourth wiring formation surface 44b formed in a step on a center axis X side by a predetermined height H with respect to the third wiring formation surface 44a.

Note that in the distal end barrel member 21, two inside lands 52b and 53b are formed on the third wiring formation surface 44a, and two outside lands 51b and 54b are formed on the fourth wiring formation surface 44b here. The two lands 51b and 54b and the two lands 52b and 53b are formed in such a manner that axes Y1 and Y2 passing through centers are deviated from each other by a predetermined distance L1 in a front-back direction along a center axis X.

Note that the two outside lands 51b and 54b may be formed on the third wiring formation surface 44a, the two inside lands 52b and 53b may be formed on the fourth wiring formation surface 44b, or the four lands 51b to 54b may be formed in a staggered manner in a direction orthogonal to the center axis X.

By adopting the configuration like this, it is possible to more enhance workability of connection of respective core wires 61a to 64a of four cables 61 to 64 by soldering or the like because the four lands 51b to 54b are in positions deviated in two directions orthogonal to the center axis X, an up-down direction and a left-right direction here.

Since distances of connection portions of the four cables 61 to 64 can be taken to be long, the four cables 61 to 64 are less susceptible to noise from one another.

Second Embodiment

Next, an endoscope 1 of one aspect according to a second embodiment of the present invention is described based on the drawings. Concerning explanation of the endoscope 1 of the present embodiment, with respect to the components described in the first embodiment, detailed explanation of the components is omitted, and the same reference signs are used.

Figure 15:
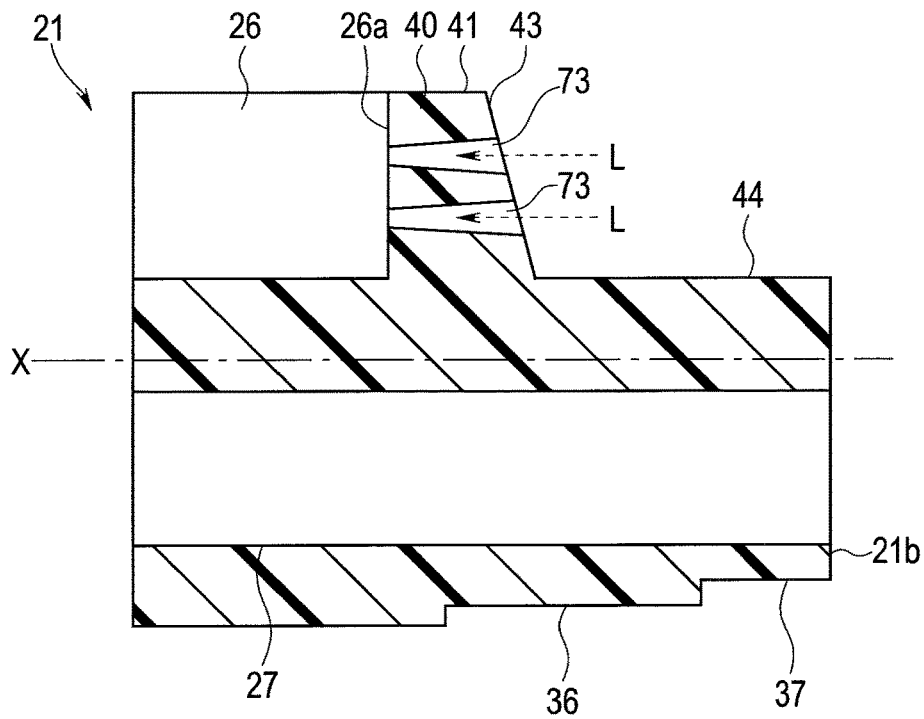
FIG. 15 is a cross-sectional view showing a configuration of a distal end barrel member in which through-holes are formed according to a second embodiment of the present invention.

As shown in FIG. 15, in a distal end barrel member 21 provided at a distal end portion 6 of an insertion portion 2 of the endoscope 1 of the present embodiment, four through-holes 73 here that penetrate to a mounting surface 26a of a module accommodation chamber 26 are formed by irradiating laser light L that activates a specified area surface of a circuit pattern along a center axis X from a proximal end side toward a second wiring formation surface 43 that is an inclined surface located on a proximal end side of a wall portion 40.

Note that the four through-holes 73 are irradiated with the laser light L substantially parallel to the center axis X from the second wiring formation surface 43, and therefore each of the through-holes 73 becomes a hole portion in a substantially cone shape in which a hole diameter on a second wiring formation surface 43 side is large, and a hole diameter on a mounting surface 26a side is small. In other words, the through-hole 73 is a hole portion tapering to a distal end side and having a hole axis parallel to the center axis X of the distal end barrel member 21.

Figure 16:
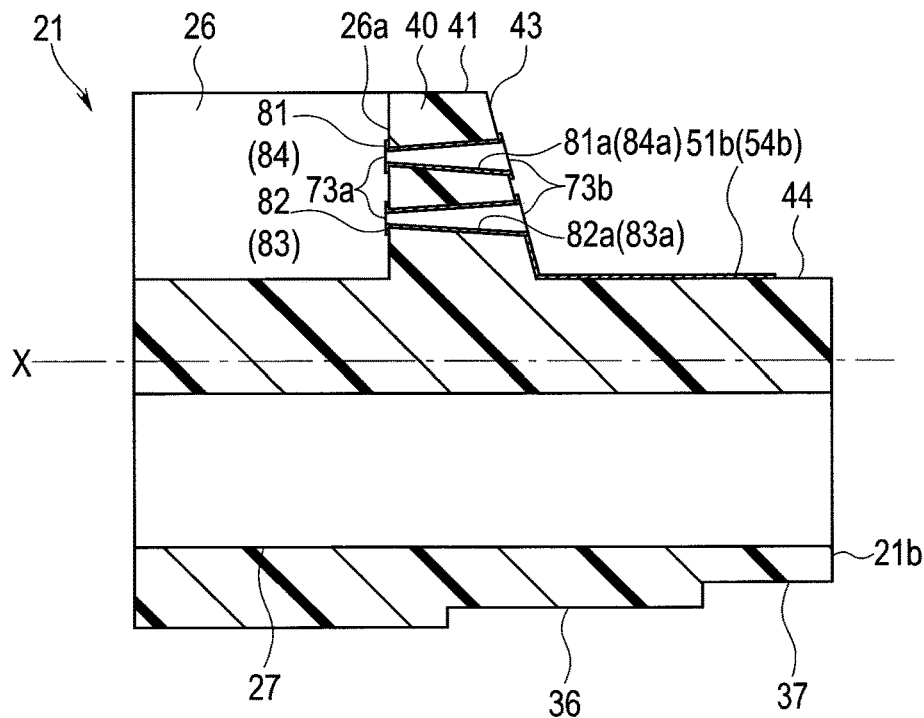
FIG. 16 is a cross-sectional view showing the configuration of the distal end barrel member according to the second embodiment of the present invention.

In the distal end barrel member 21, a metal coating film is also deposited on inner peripheral surfaces of the four through-holes 73 the surfaces of which are activated during electroless plating treatment for metal pattern formation, and four through-electrodes 81a to 84a are formed as shown in FIG. 16. The four through-electrodes 81a to 84a respectively have distal end openings 73a having the same diameters and proximal end openings 73b having the same diameters.

Note that the four through-electrodes 81a to 84a each have a tapering tube shape having a hole axis parallel to the center axis X of the distal end barrel member 21, in which the distal end opening 73a has a small diameter, and the proximal end opening 73b has a large diameter, conforming to the shapes of the through-holes 73.

Figure 17:
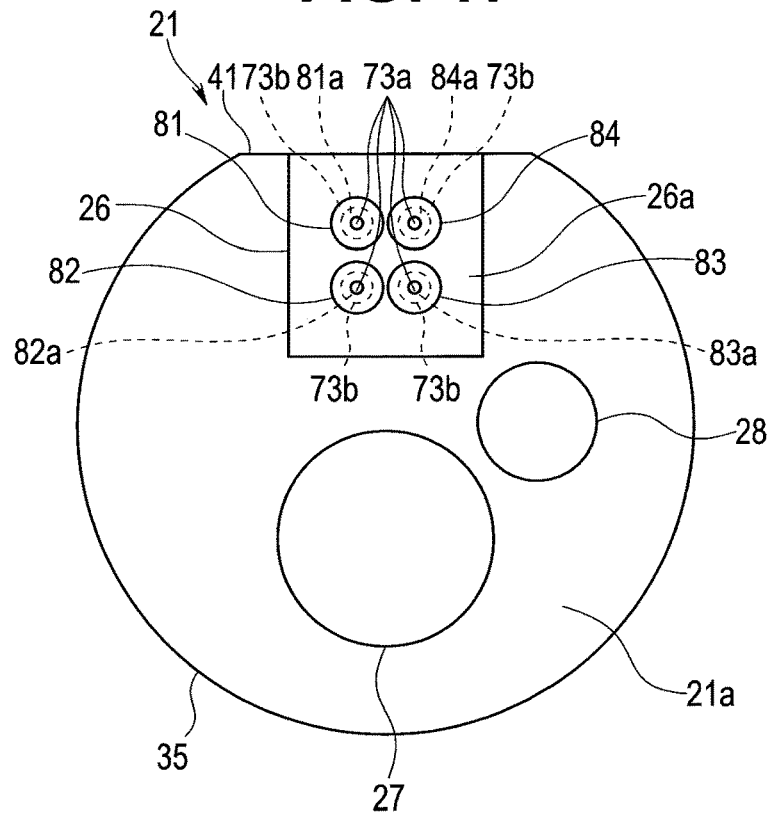
FIG. 17 is a front view showing the configuration of the distal end barrel member according to the second embodiment of the present invention.

As shown in FIG. 17, in the distal end barrel member 21, four contact lands 81 to 84 each in a circular ring shape that electrically continue to the through-electrodes 81a to 84a respectively are pattern-formed on the mounting surface 26a of the module accommodation chamber 26. To the four contact lands 81 to 84, four terminals 33a that are electric contacts of a camera module 30 are electrically connected.

Figure 18:
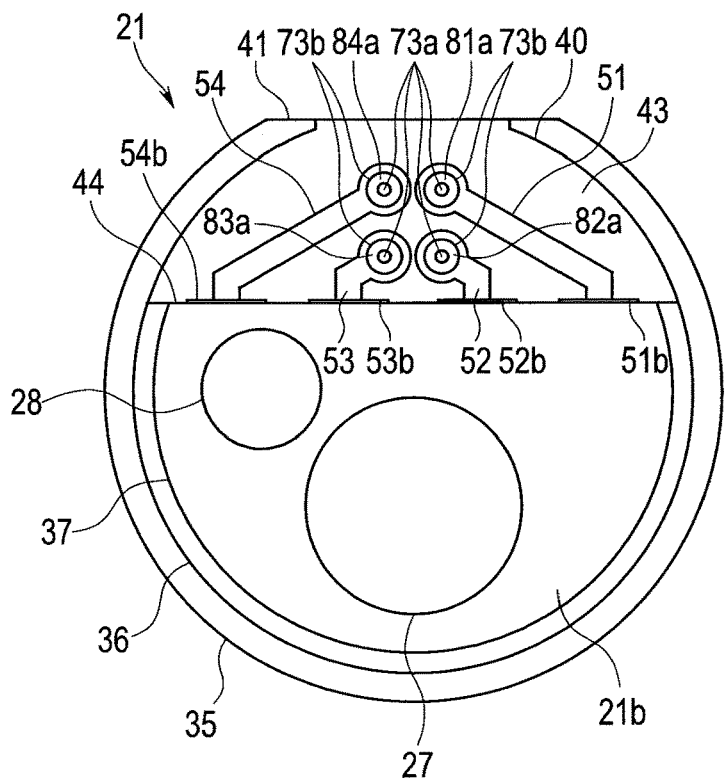
FIG. 18 is a back view showing the configuration of the distal end barrel member according to the second embodiment of the present invention.

As shown in FIG. 18, in the distal end barrel member 21, four wiring patterns 51 to 54 that are conductive paths respectively electrically continue to the through-electrodes 81a to 84a are pattern-formed on the second wiring formation surface 43 and a third wiring formation surface 44, and the four wiring patterns 51 to 54 are also caused to electrically continue to four lands 51b to 54b on the third wiring formation surface 44.

In each of the four through-electrodes 81a to 84a, the proximal end opening 73b has a larger cross-sectional shape than the distal end opening 73a, so that an interval on the second wiring formation surface 43 side is disposed to be wider than a terminal 33a interval (width between the terminals 33a) of the camera module 30.

The four through-electrodes 81a to 84a increase and widen intervals among the four lands 51b to 54b electrically continuing via the four wiring patterns 51 to 54 and formed on the third wiring formation surface 44, and thereby connection of core wires 61a to 64a of the cables 61 to 64 by soldering or the like becomes easy.

In this way, in the distal end barrel member 21 of the present embodiment, it is possible to shorten a distance between the four contact lands 81 to 84 on the mounting surface 26*a* of the module accommodation chamber 26 and the four lands 51*b* to 54*b* of the third wiring formation surface 44 more than in the configuration of the first embodiment, by providing the four through-electrodes 81*a* to 84*a* in the wall portion 40. Thereby, resistance to electric noise from surroundings is enhanced.

The four through-electrodes 81*a* to 84*a* that are one of conductive paths that sends and receives signals to and from the camera module 30 that is an imager unit are formed on a center axis X side that is an inside diameter direction of the distal end barrel member 21, and are far from an outer surface of the distal end portion 6 of the insertion portion 2, so that the four through-electrodes 81*a* to 84 are less susceptible to electric noise from the surroundings. Accordingly, in the endoscope 1 of the present embodiment, it is possible to make the camera module 30 mounted in the distal end barrel member 21 less susceptible to electric noise from the surroundings.

Since the four through-holes 73 in the wall portion 40 of the distal end barrel member 21 is bored by the laser light L when surface activation is performed when a metal pattern is formed by using the MID technology, the number of steps at a time of work can be decreased.

Note that the laser light L is irradiated to the positions to form the four through-holes 73 and positions to form the wiring patterns 51 to 54 here, and work efficiency is improved by making an irradiation direction of the laser light L only one direction from the proximal end side, and making an irradiation angle of the laser light forming the four through-holes 73 the same.

First Modification

Figure 19:
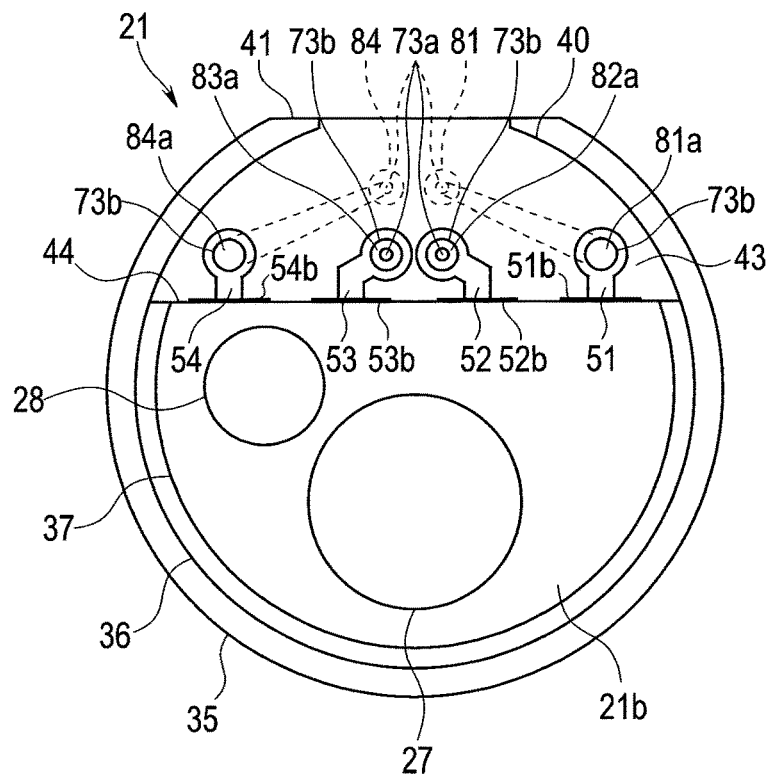
FIG. 19 is a back view showing a configuration of a distal end barrel member according to a first modification of the second embodiment of the present invention.
Figure 20:
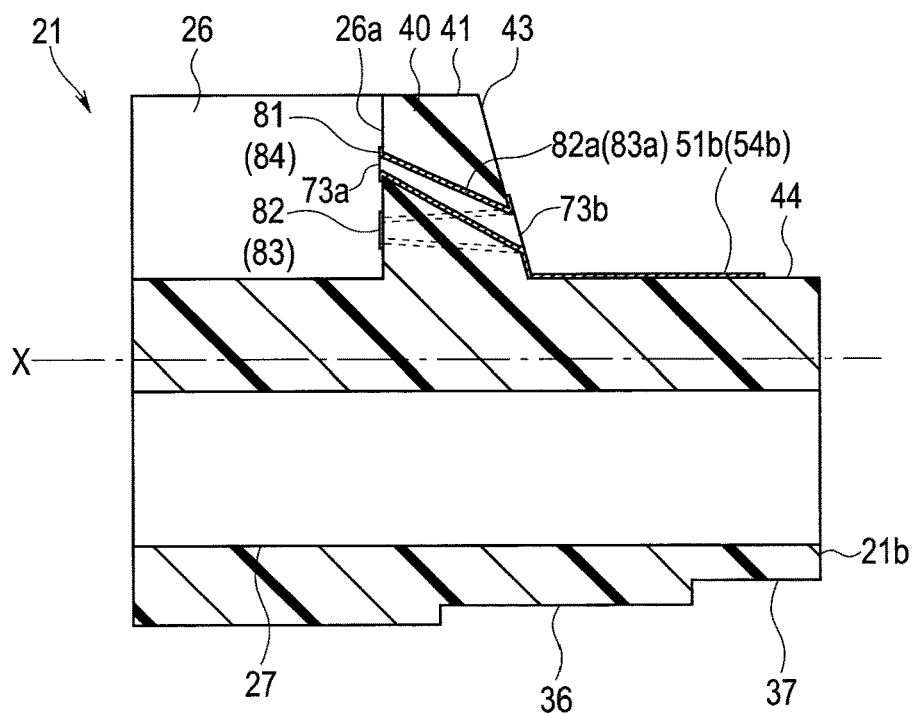
FIG. 20 is a cross-sectional view showing the configuration of the distal end barrel member according to the first modification of the second embodiment of the present invention.

As shown in FIG. 19 and FIG. 20, in four through-electrodes 81*a* to 84*a*, proximal end openings 73*b* provided in the second wiring formation surface 43 may be disposed in a line in a lateral direction. Thereby, the wall portion 40 of the distal end barrel member 21 in a height direction (one outer peripheral direction of the distal end barrel member 21) can be restrained to be low, and increase in size of the outside diameter of the distal end portion 6 can be restrained. In other words, the through-electrodes 81*a* and 84*a* on both sides are formed upward with a predetermined angle to the center axis X of the distal end barrel member 21.

Note that in each of two contact lands 81 and 84 on an upper side that are provided on a mounting surface 26*a* of a module accommodation chamber 26, heights of upper ends of a distal end opening 73*a* and a proximal end opening 73*b* may be formed to be substantially the same, and thereby, it is possible to restrain increase in diameter of the distal end barrel member 21 by restraining an influence on the outside diameter while preventing interference between two contact lands 81 and 84 and between wiring patterns 51 and 54.

Second Modification

Figure 21:
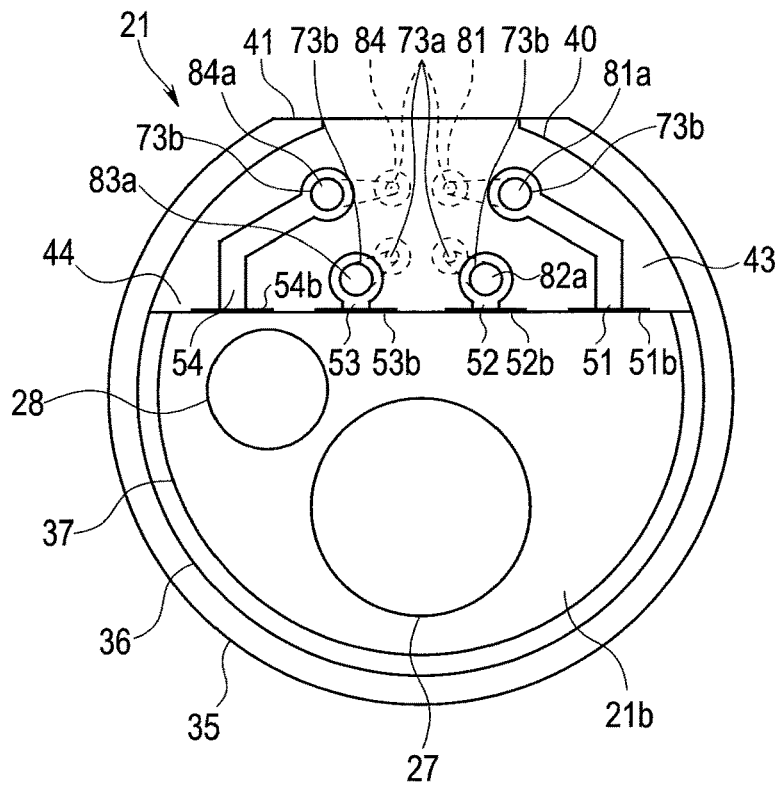
FIG. 21 is a back view showing a configuration of a distal end barrel member according to a second modification of the second embodiment of the present invention.
Figure 22:
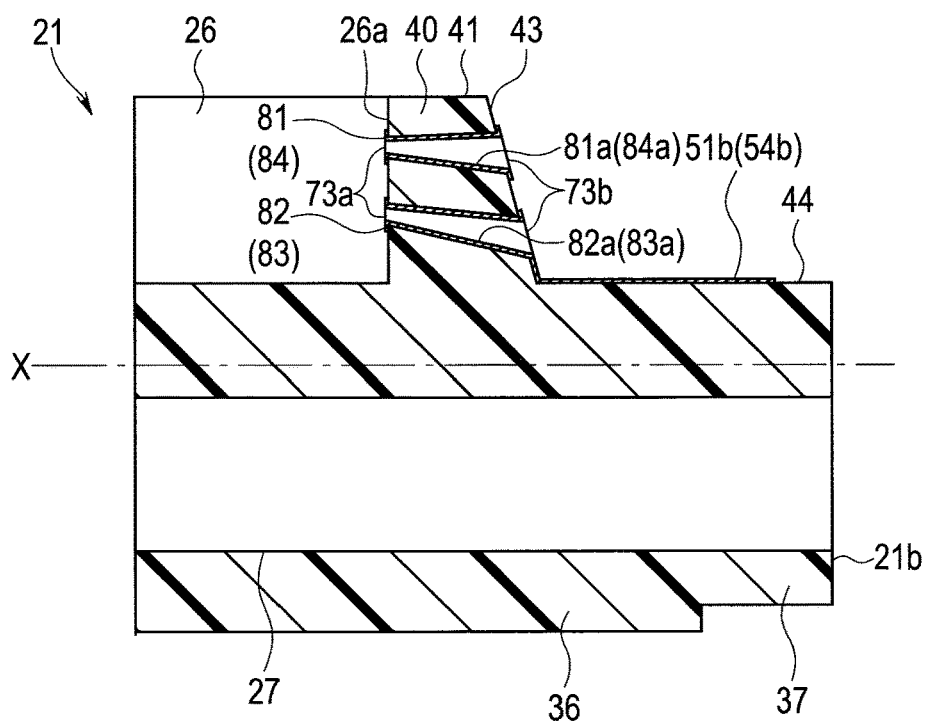
FIG. 22 is a cross-sectional view showing the configuration of the distal end barrel member according to the second modification of the second embodiment of the present invention.

As shown in FIG. 21 and FIG. 22, four through-electrodes 81*a* to 84*a* may be disposed so that intervals among proximal end openings 73*b* of a second wiring formation surface 43 increase. In other words, the four through-electrodes 81*a* to 84*a* are formed so that center separation distances of the respective proximal end openings 73*b* become long.

In addition, positions of the proximal end openings 73*b* may be determined so that lengths in a longitudinal direction of the four through-electrodes 81*a* to 84*a* become substantially the same. In the four through-electrodes 81*a* to 84*a*, by matching the lengths in the longitudinal direction, it is possible to make diameters of opening holes on an incident side formed by the laser light L constant, and it is also possible to make diameters of the four proximal end openings 73*b* substantially the same.

As for the laser light L forming through-hole 73, an irradiation position to the second wiring formation surface 43 that is an inclined surface on a proximal end side of a wall portion 40 inclines with respect to a center axis X of a distal end barrel member 21, and the laser light L is irradiated in an outside diameter direction to be away from the center axis X toward a distal end side.

Two upper through-holes 73 and two lower through-holes 73 differ in angle inclining with respect to the center axis X. and are formed so that directions of inclination of two through-holes 73 on a left and a right are opposite.

The four through-electrodes 81*a* to 84*a* are formed in directions corresponding to inclinations of the through-holes 73 in which the respective four through-electrodes 81*a* to 84*a* are formed.

By forming two on the upper side of the proximal end openings 73*b* of the four through-electrodes 81*a* to 84*a* so that heights of upper ends are made substantially the same as heights of upper ends of distal end openings 73*a*, or the heights of the upper ends become lower to the center axis X side that is an inside diameter direction of the distal end barrel member 21, it is possible to restrain increase in diameter of the distal end barrel member 21 by restraining an influence on the outside diameter while preventing interference between two contact lands 81 and 84 and between wiring patterns 51 and 54.

Third Modification

Figure 23:
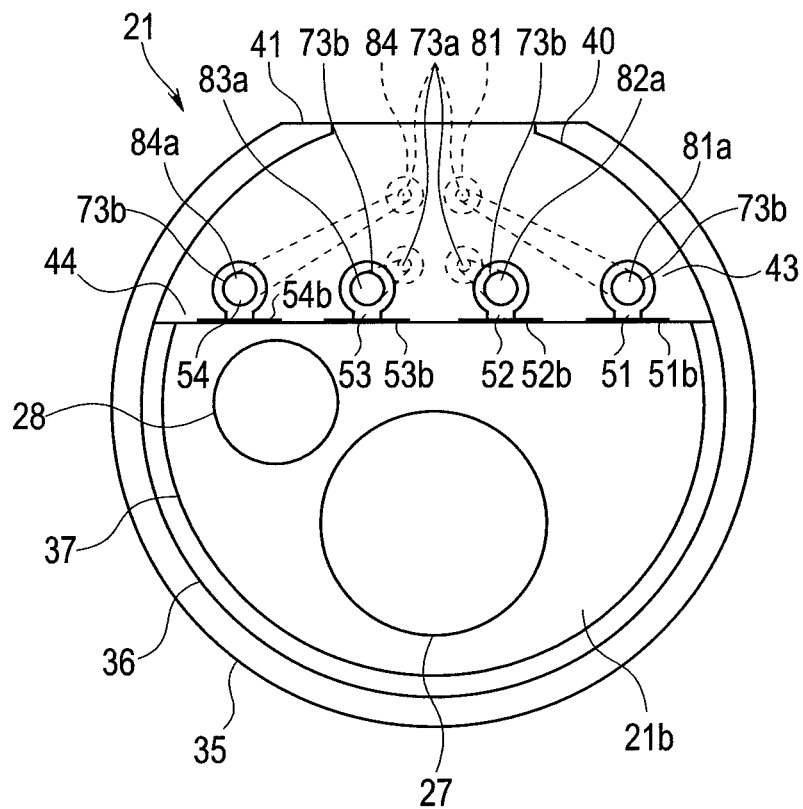
FIG. 23 is a back view showing a configuration of a distal end barrel member according to a third modification of the second embodiment of the present invention.
Figure 24:
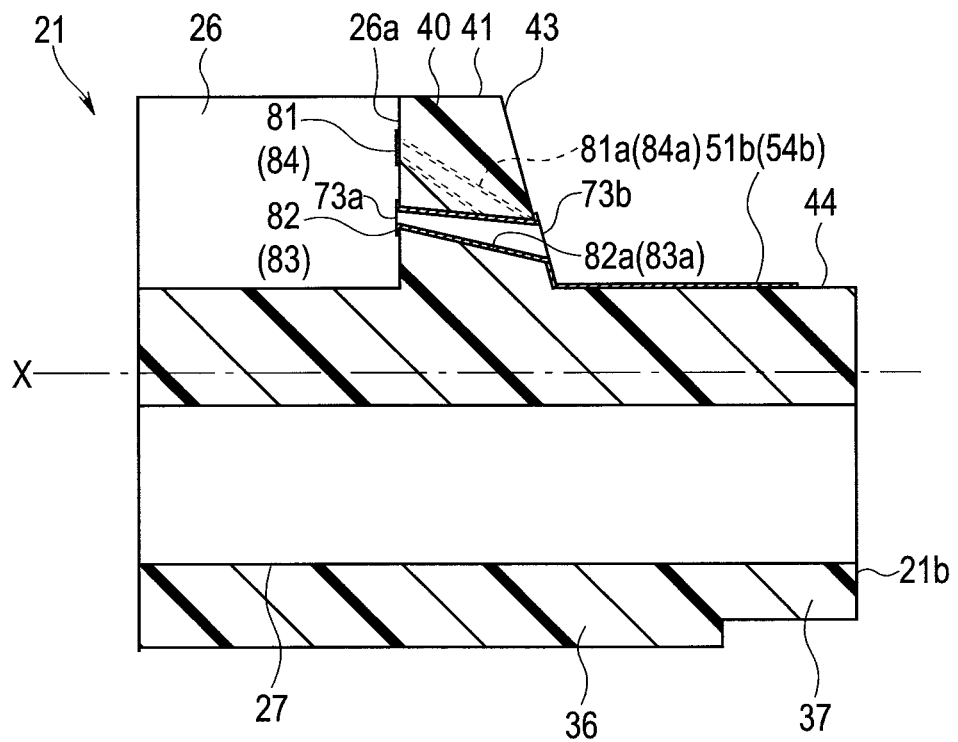
FIG. 24 is a cross-sectional view showing the configuration of the distal end barrel member according to the third modification of the second embodiment of the present invention.

As shown in FIG. 23 and FIG. 24, four through-electrodes 81*a* to 84*a* may be disposed in a line in a lateral direction so that intervals of proximal end openings 73*b* of a second wiring formation surface 43 become large. Here, as for laser light L that forms a through-hole 73, an irradiation position to the second wiring formation surface 43 that is an inclined surface on a proximal end side of a wall portion 40 also inclines with respect to a center axis X of a distal end barrel member 21, and the laser light L is irradiated in an outside diameter direction to be away from the center axis X toward a distal end side.

Two upper through-holes 73 and two lower through-holes 73 differ in angle inclining with respect to the center axis X, and are formed so that directions of inclinations of two through-holes 73 on a left and a right become opposite. The four through-electrodes 81*a* to 84*a* are formed in directions corresponding to inclinations of the through-holes 73 in which the four through-electrodes 81*a* to 84*a* are formed.

In the distal end barrel member 21 here, the wall portion 40 in a height direction can be reduced to be low, and increase in diameter of the distal end barrel member 21 can be restrained, by disposing the proximal end openings 73*b* of the four through-electrodes 81*a* to 84*a* in a line.

Fourth Modification

Figure 25:
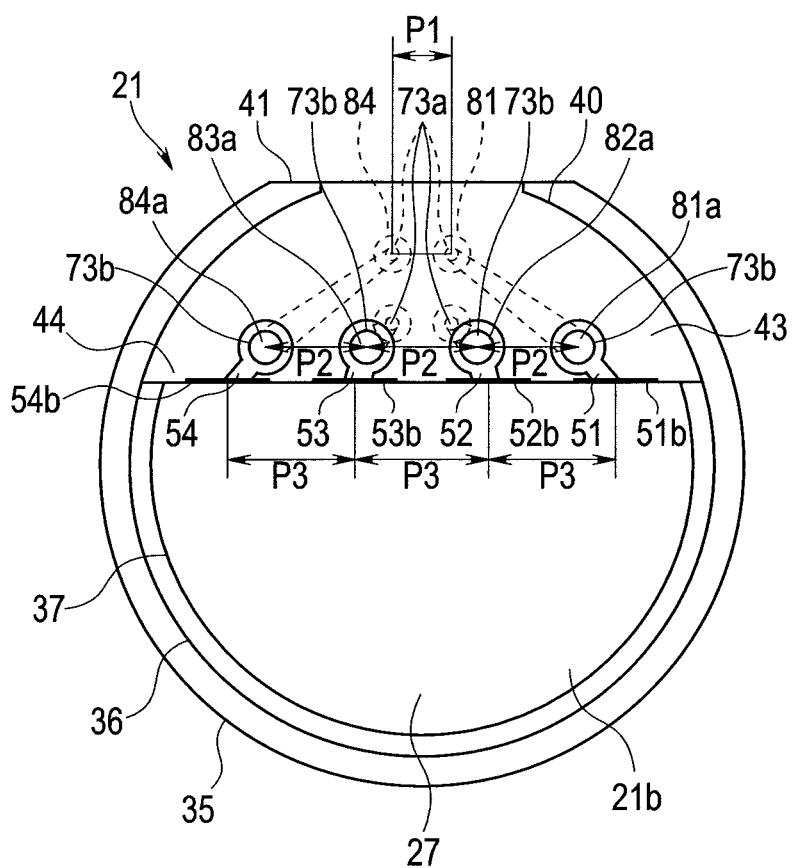
FIG. 25 is a back view showing a configuration of a distal end barrel member according to a fourth modification of the second embodiment of the present invention.

As shown in FIG. 25, a height of a wall portion 40 of a distal end barrel member 21 can be reduced to be low, and a difference in length in a longitudinal direction of four through-electrodes 81*a* to 84*a* can be reduced, by forming the four through-electrodes 81*a* to 84*a* so that an interval (pitch) P2 between proximal end opening 73*b* centers is increased with respect to an interval (pitch) P1 of distal end opening 73a centers, and becomes smaller than an interval (pitch) P3 of centers of four lands 51b to 54b on a third wiring formation surface 44 (P1<P2<P3).

Fifth Modification

Figure 26:
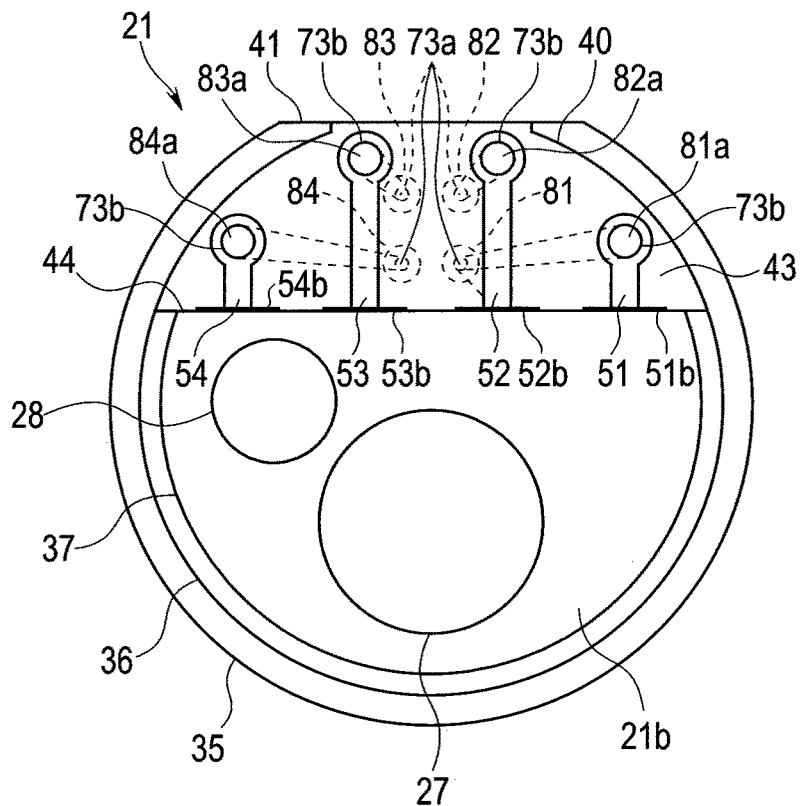
FIG. 26 is a back view showing a configuration of a distal end barrel member according to a fifth modification of the second embodiment of the present invention.
Figure 27:
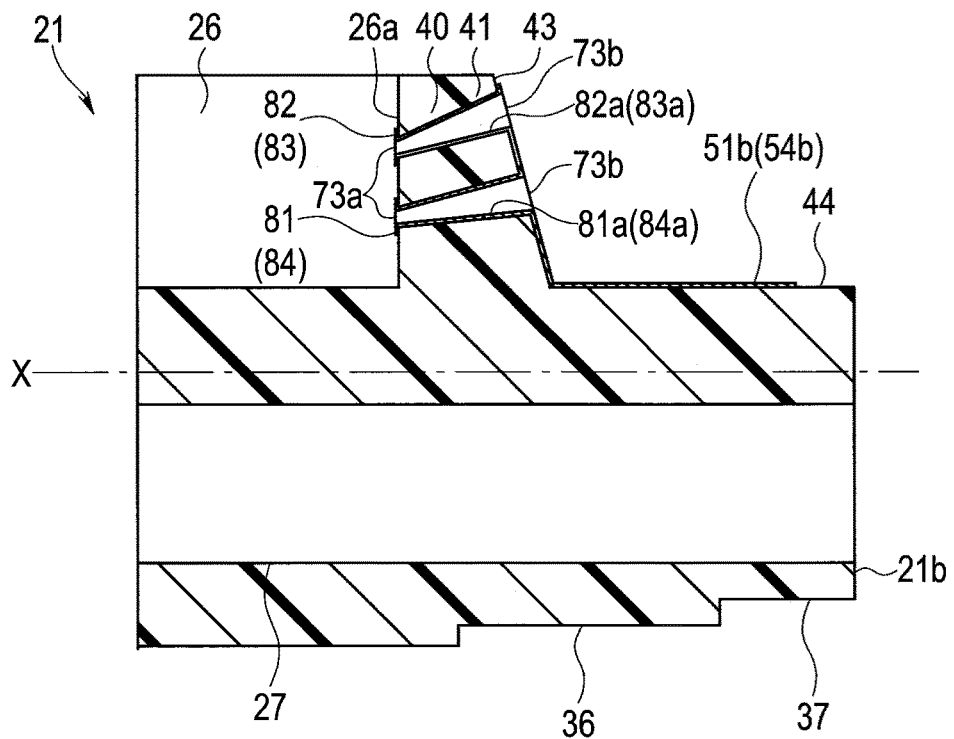
FIG. 27 is a cross-sectional view showing the configuration of the distal end barrel member according to the fifth modification of the second embodiment of the present invention.

As shown in FIG. 26 and FIG. 27, in each of four through-electrodes 81a to 84a, a proximal end opening 73b of a second wiring formation surface 43 may be disposed on an upper side in a height direction from a distal end opening 73a In other words, the four through-electrodes 81a to 84a are formed to incline in a center axis X direction of a distal end barrel member 21 from a proximal end side to a distal end side.

As for laser light L that forms a through-hole 73 here, an irradiation position to the second wiring formation surface 43 that is an inclined surface on the proximal end side of a wall portion 40 inclines with respect to a center axis X of the distal end barrel member 21, and the laser light L is irradiated in an inside diameter direction to be close to the center axis X toward the distal end side.

Thereby, when the through-hole 73 is formed, the laser light L can be irradiated diagonally from above on the proximal end side to below, so that it is possible to prevent other sites of the distal end barrel member 21 from being irradiated by considering an irradiation direction in which the laser light L can be irradiated to only the wall portion 40.

Sixth Modification

Figure 28:
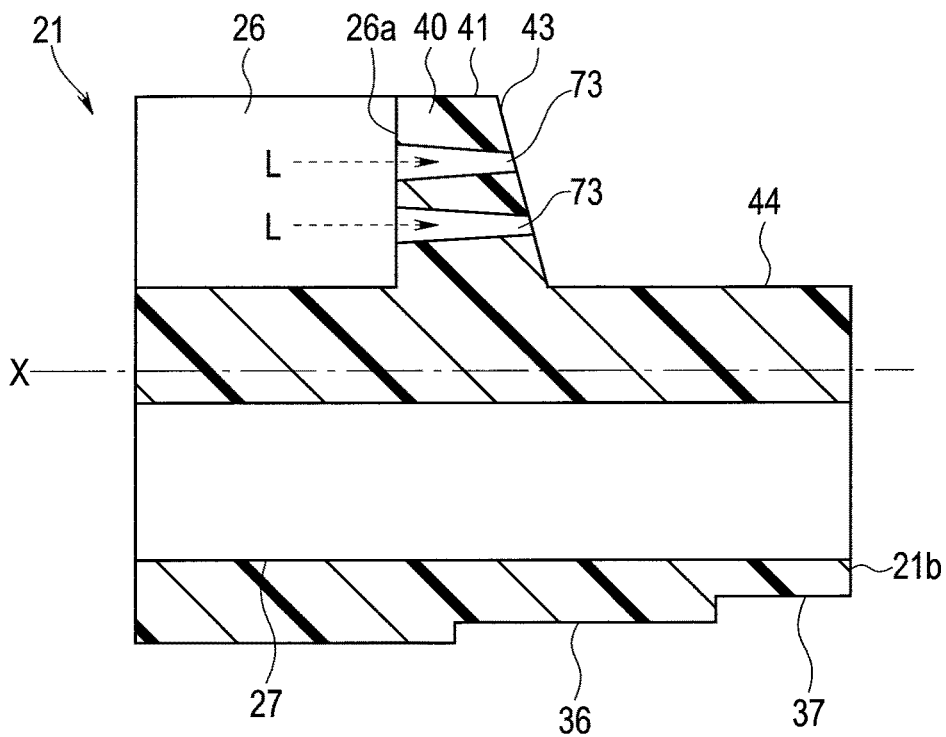
FIG. 28 is a cross-sectional view showing a configuration of a distal end barrel member in which through-holes are formed according to a sixth modification of the second embodiment of the present invention.

As shown in FIG. 28, four through-holes 73 may be formed by irradiating laser light L from a distal end side of a distal end barrel member 21 to a mounting surface 26a of a module accommodation chamber 26. Note that the laser light L here is irradiated substantially parallel to a center axis X of the distal end barrel member 21.

Figure 29:
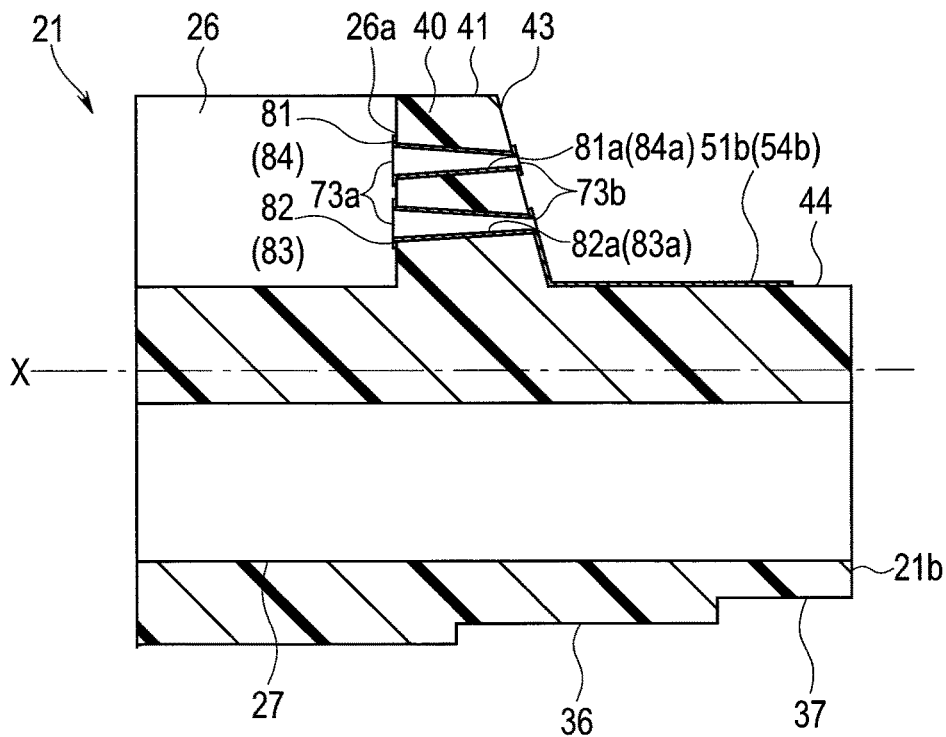
FIG. 29 is a cross-sectional view showing the configuration of the distal end barrel member according to the sixth modification of the second embodiment of the present invention.

As shown in FIG. 29, four through-electrodes 81a to 84a are formed in the four through-holes 73 that are formed in a wall portion 40. The four through-electrodes 81a to 84a here are each in a cone shape in which a diameter becomes narrower toward a proximal end direction.

Figure 30:
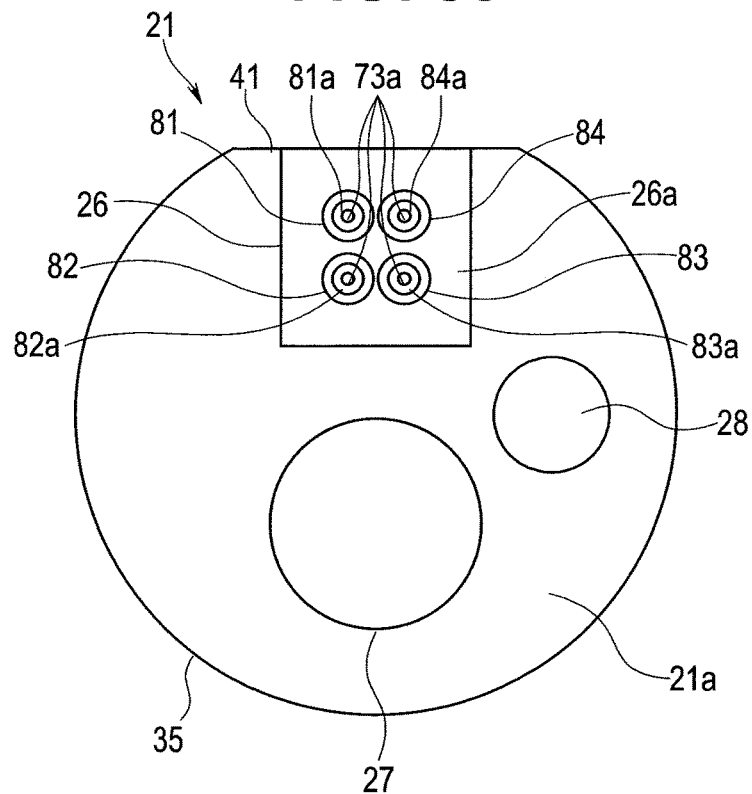
FIG. 30 is a front view showing the configuration of the distal end barrel member according to the sixth modification of the second embodiment of the present invention.
Figure 31:
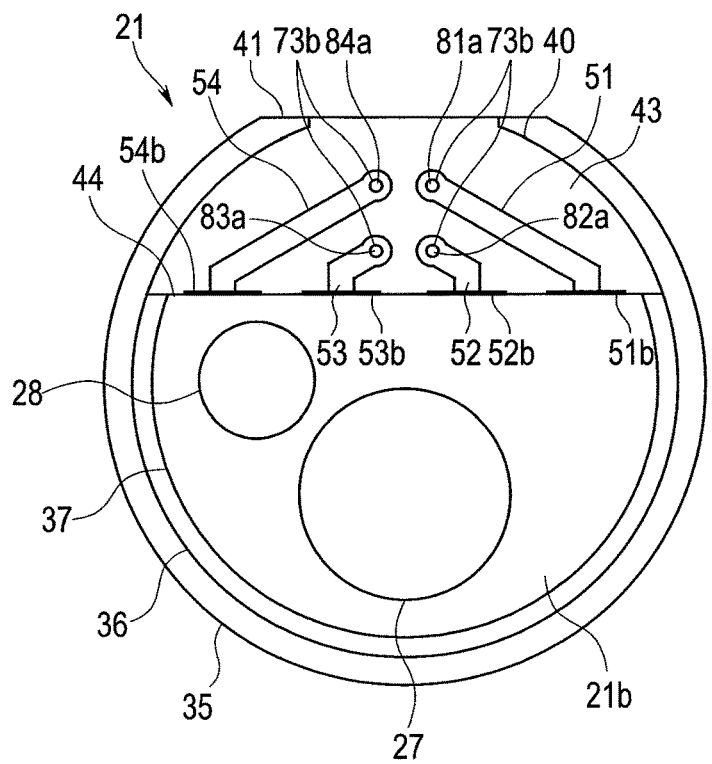
FIG. 31 is a back view showing the configuration of the distal end barrel member according to the sixth modification of the second embodiment of the present invention.

In other words, in the four through-electrodes 81a to 84a, distal end openings 73a of the mounting surface 26a become large as shown in FIG. 30, and proximal end openings 73b of a second wiring formation surface 43 become small as shown in FIG. 31.

Since irradiation of the laser light L at a time of formation of the four through-electrodes 81a to 84a is performed from a mounting surface 26a side of the module accommodation chamber 26 in which a camera module 30 is loaded on the distal end side, in this way, positions of contact lands 81 to 84 can be accurately formed to correspond to terminals 33a of a camera module 30.

Seventh Modification

Figure 32:
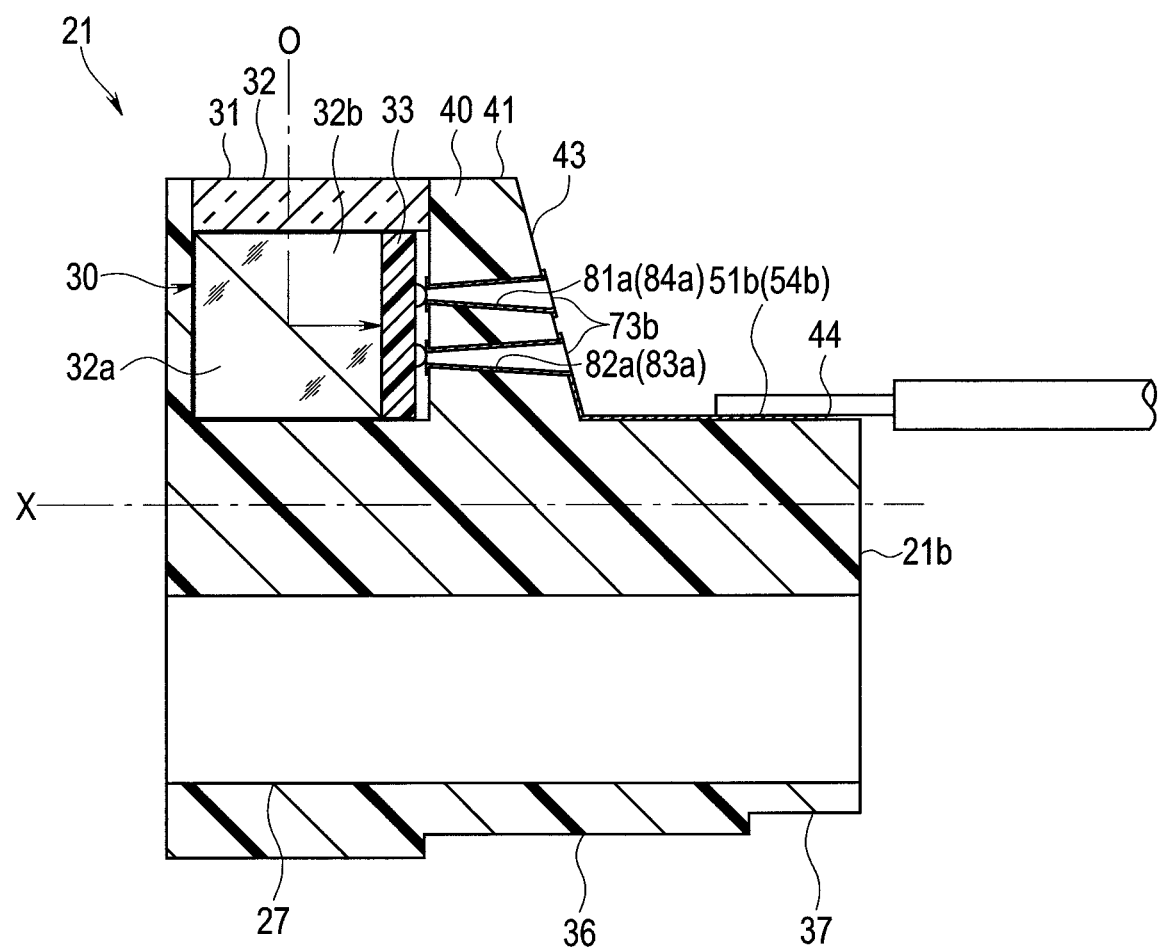
FIG. 32 is a cross-sectional view showing a configuration of a distal end barrel member on which a side-viewing camera module is loaded according to a seventh modification of the second embodiment of the present invention.

As shown in FIG. 32, a camera module 30 that is loaded on a distal end barrel member 21 may be configured to have a field of view in a direction orthogonal to a center axis X of the distal end barrel member 21. A lens unit 32 of the camera module 30 has a cover glass to be an observation window 31 provided in a side portion opening of the distal end barrel member 21, and has a prism 32a configured to reflect an optical axis O, and a protection glass 32b configured to protect a reflection surface of the prism 32a.

In other words, the endoscope 1 configures a side-viewing endoscope by being provided with the distal end barrel member 21 in which the aforementioned camera module 30 is mounted, at a distal end portion 6 of an insertion portion 2. Note that the camera module 30 may have a field of view in a direction having a predetermined angle with respect to the center axis X of the distal end barrel member 21, and may be loaded on a so-called diagonal-viewing endoscope 1.

FIG. 32 illustrates the distal end barrel member 21 with the configuration in which the four through-electrodes 81a to 84a are formed, but the side-viewing or diagonal-viewing camera module 30 can also be loaded on the distal end barrel member 21 of the first embodiment.

Eighth Modification

Figure 33:
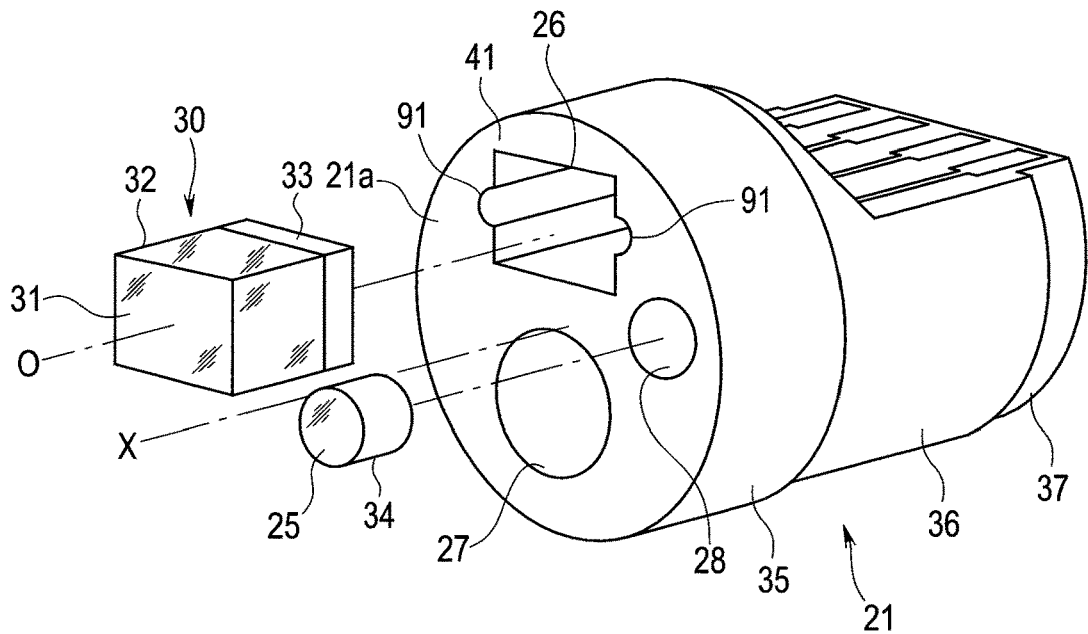
FIG. 33 is an exploded perspective view showing a configuration of a distal end barrel member according to an eighth modification of the second embodiment of the present invention.
Figure 34:
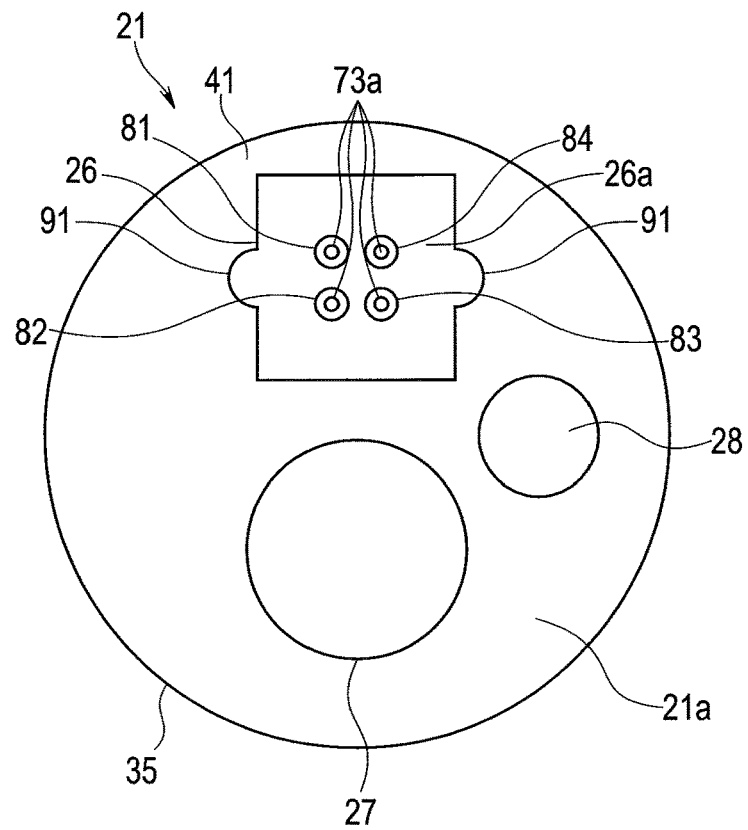
FIG. 34 is a front view showing the configuration of the distal end barrel member according to the eighth modification of the second embodiment of the present invention.

As shown in FIG. 33 and FIG. 34, a distal end barrel member 21 may be a bottomed rectangular hole portion in which a module accommodation chamber 26 loaded with a camera module 30 is opened at a distal end and a periphery is covered, with a mounting surface 26a as a bottom surface.

Note that in the module accommodation chamber 26, groove portions 91 each with an arc-shaped cross section are formed on a left and a right in a direction along a center axis X. The two groove portions 91 form gaps in which a needle (injection needle) is inserted when liquid curable resin (underfill) that fixedly attaches the camera module 30 loaded in the module accommodation chamber 26 is injected.

Figure 35:
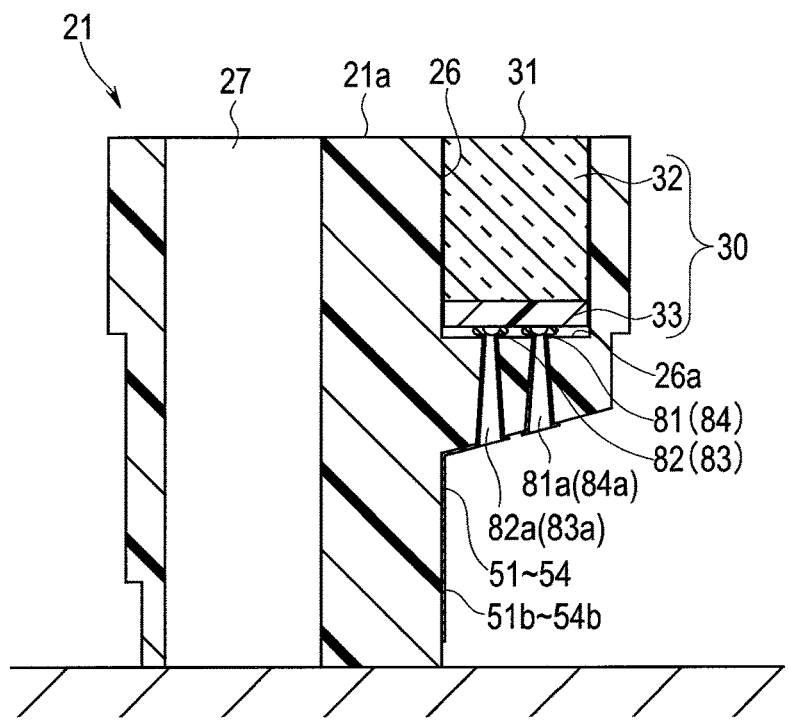
FIG. 35 is a cross-sectional view of the distal end barrel member explaining a state in which a camera module is reflow-soldered to the distal end barrel member according to the eighth modification of the second embodiment of the present invention.

Note that in the distal end barrel member 21, a distal end surface 21a side is vertically above as shown in FIG. 35, when the camera module 30 is loaded, and electrical connection of terminals 33a of the camera module 30 and four contact lands 81 to 84 on the mounting surface 26a is reflow-soldered. At this time, the camera module 30 is stably placed on the mounting surface 26a in the module accommodation chamber 26.

Since four through-electrodes 81a to 84a that are formed in the distal end barrel member 21 are in tube shapes having distal end openings 73a, solder required for bonding to the terminals 33a of the camera module 30 flows into insides of the through-electrodes 81a to 84a during reflow-soldering, and poor electrical connection, poor mechanical coupling and the like are likely to occur.

Figure 36:
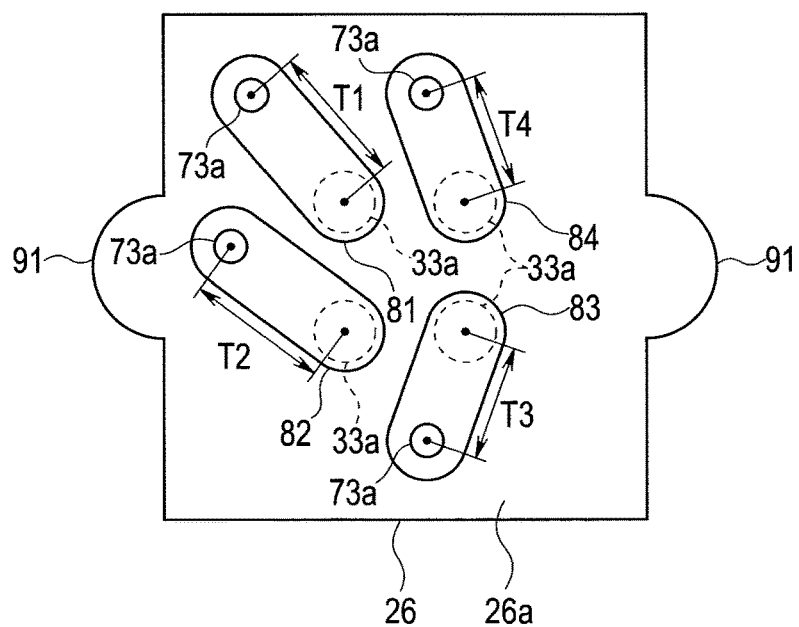
FIG. 36 is a plan view showing a configuration of a mounting surface of a module accommodation chamber according to the eighth modification of the second embodiment of the present invention.

Accordingly, the four contact lands 81 to 84 that are formed on the mounting surface 26a of the module accommodation chamber 26 are preferably in shapes in which the distal end openings 73a are provided at positions separated by predetermined distances T1 to T4 from sites at which the terminals 33a of the camera module 30 are soldered, as shown in FIG. 36.

Ninth Modification

Figure 37:
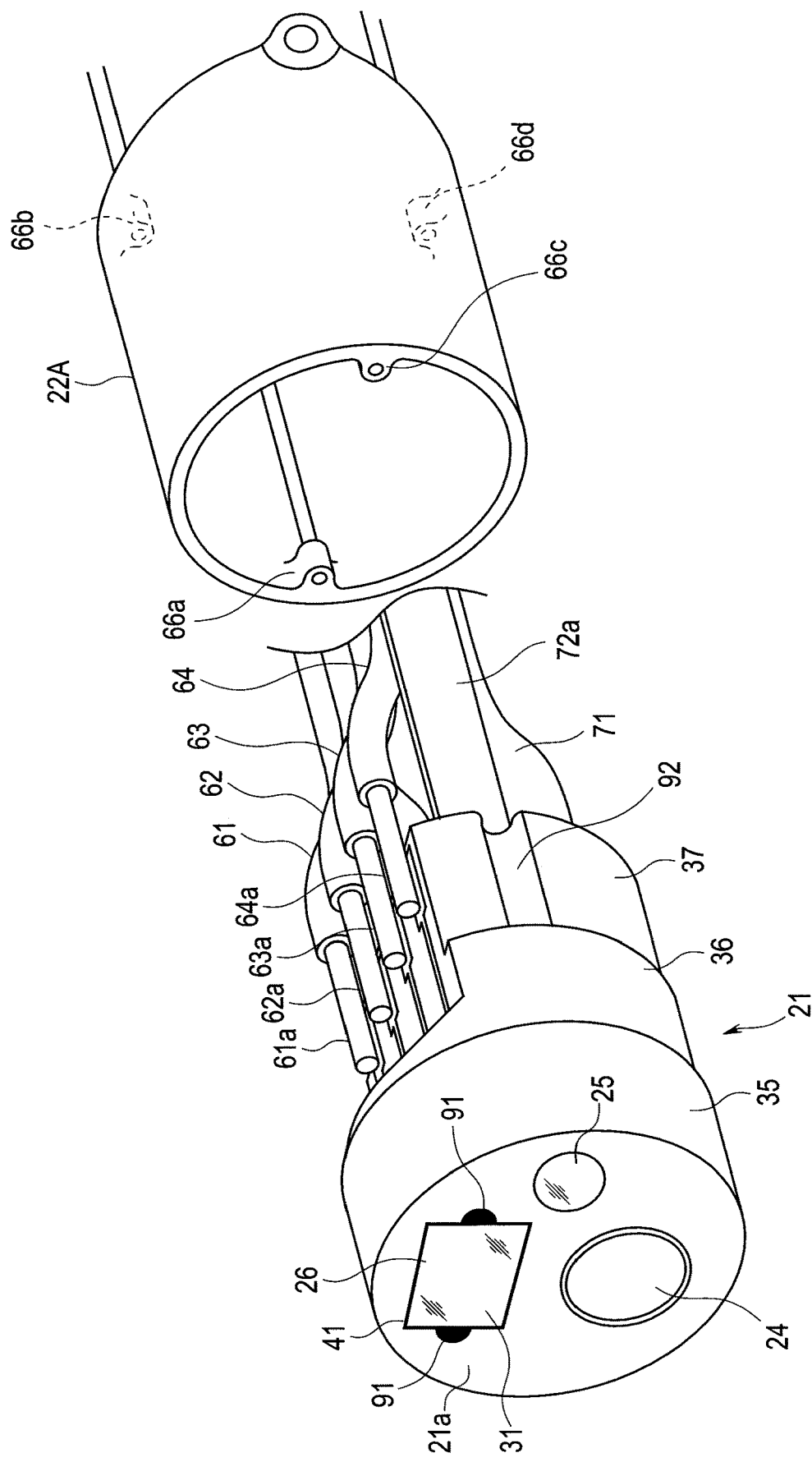
FIG. 37 is an exploded perspective view showing a configuration of a distal end barrel member and a bending piece according to a ninth modification of the second embodiment of the present invention.

As shown in FIG. 37, in a distal end barrel member 21, relief grooves 92 configured to accommodate two wire fixing portions 66a and 66c provided on the left and right of a distal end portion of a bending piece 22A at a distalmost end here may be formed in a second small diameter portion 37 that is fitted to the distal end bending piece 22A.

Figure 38:
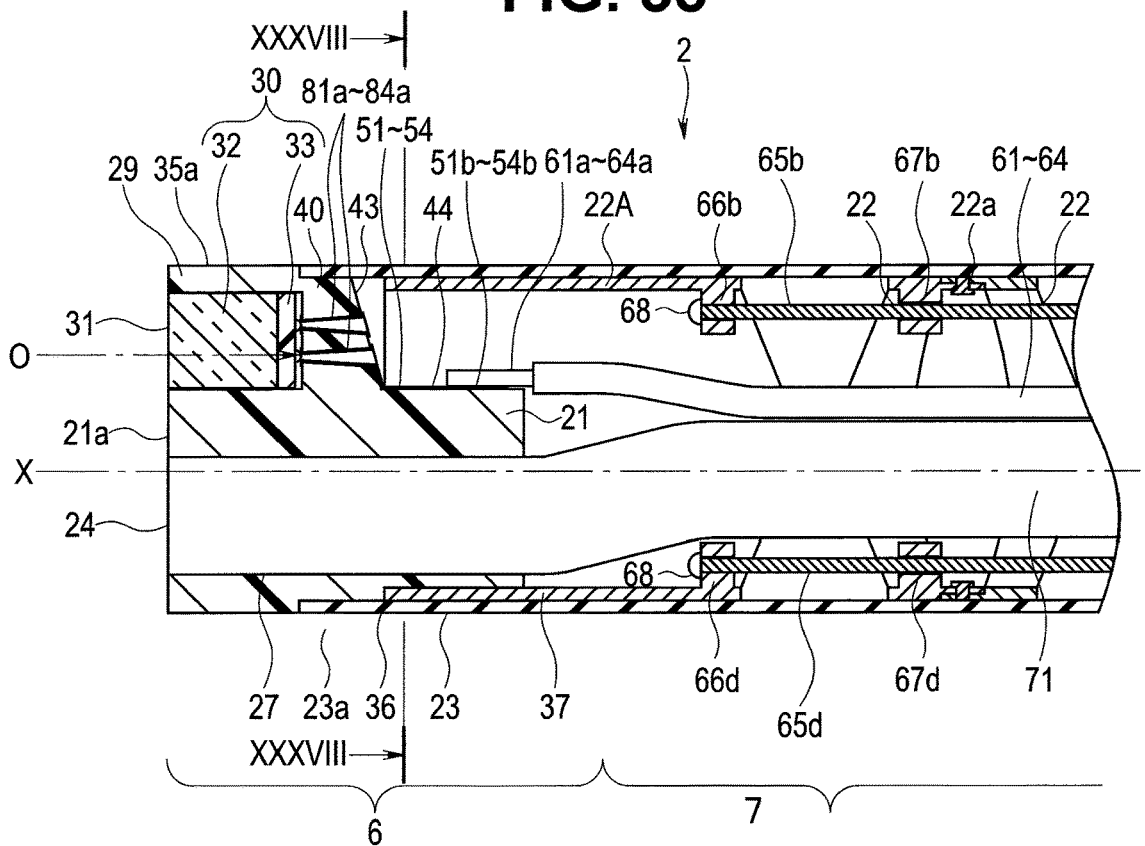
FIG. 38 is a cross-sectional view showing a configuration of a distal end portion of an insertion portion according to the ninth modification of the second embodiment of the present invention.
Figure 39:
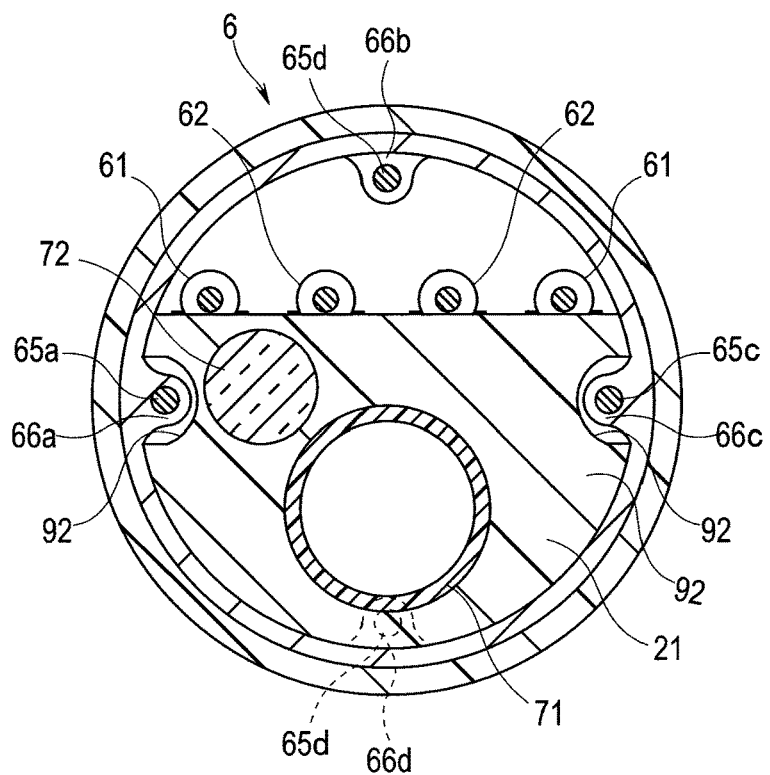
FIG. 39 is a cross-sectional view showing a configuration of a distal end portion along line XXXVIII-XXXVIII in FIG. 38 according to the ninth modification of the second embodiment of the present invention.

As shown in FIG. 38 and FIG. 39, the bending piece 22A at a distalmost end here is configured to be provided with four wire fixing portions 66a to 66d in an up-down and left-right directions. The two wire fixing portions 66a and 66c are disposed on a distal end side, and the two wire fixing portions 66b and 66d are disposed on a proximal end side. In other words, the two wire fixing portions 66a and 66c and the two wire fixing portions 66b and 66d are provided at opposite positions that rotate 180° around the center axis X, respectively.

In other words, the wire fixing portions 66a to 66d in a direction adjacent around a circumference of the bending piece 22A are provided at different positions rotated by 90° around the center axis X at substantially equal intervals in order. Note that the bending piece 22A is provided with wire guides 67a to 67d in the up-down and left-right directions similarly.

In the bending piece 22A at the distalmost end, the two wire fixing portions 66b and 66d in the up-down direction are provided at a proximal end portion.

The relief grooves 92 configured to accommodate the two wire fixing portions 66a and 66c of the bending piece 22A are provided in the distal end barrel member 21, and thereby positioning in the up-down and left-right directions around the center axis X can be easily performed at a time of fitting of the distal end barrel member 21 and the bending piece 22A.

Note that in four cables 61 to 64, connection portions to four lands 51b to 54b on a third wiring formation surface 44 are provided at substantially the same position as the two wire fixing portions 66a and 66c that are accommodated in the relief grooves 92 at a distal end side, in a center axis X direction (position orthogonal to the center axis X).

Accordingly, the distal end barrel member 21 is configured to be able to secure connection strength with the bending piece 22A without increasing a length of a distal end portion 6 to be a rigid portion of an insertion portion 2, by fitting a length in the center axis X direction of the second small diameter portion 37 on which the lands 51b to 54b are formed into the bending piece 22A at the distalmost end.

It is possible to enhance hermeticity (water tightness) in the distal end barrel member 21 by bonding and fixing fitting portions of the second small diameter portion 37 and the bending piece 22A. Thereby, it is possible to secure electric insulation of the connection portions of the four cables 61 to 64 and the four lands 51b to 54b, and the like.

The second small diameter portion 37 including the connection portions of the four cables 61 to 64 and the lands 51b to 54b on the third wiring formation surface 44 is bonded and fixed to the bending piece 22A that is fitted. In this state, the two wire fixing portions 66a and 66c and the relief grooves 92 are also bonded and fixed, so that bonding strength of the distal end barrel member 21 and the bending piece 22A can be enhanced.

Tenth Modification

Figure 40:
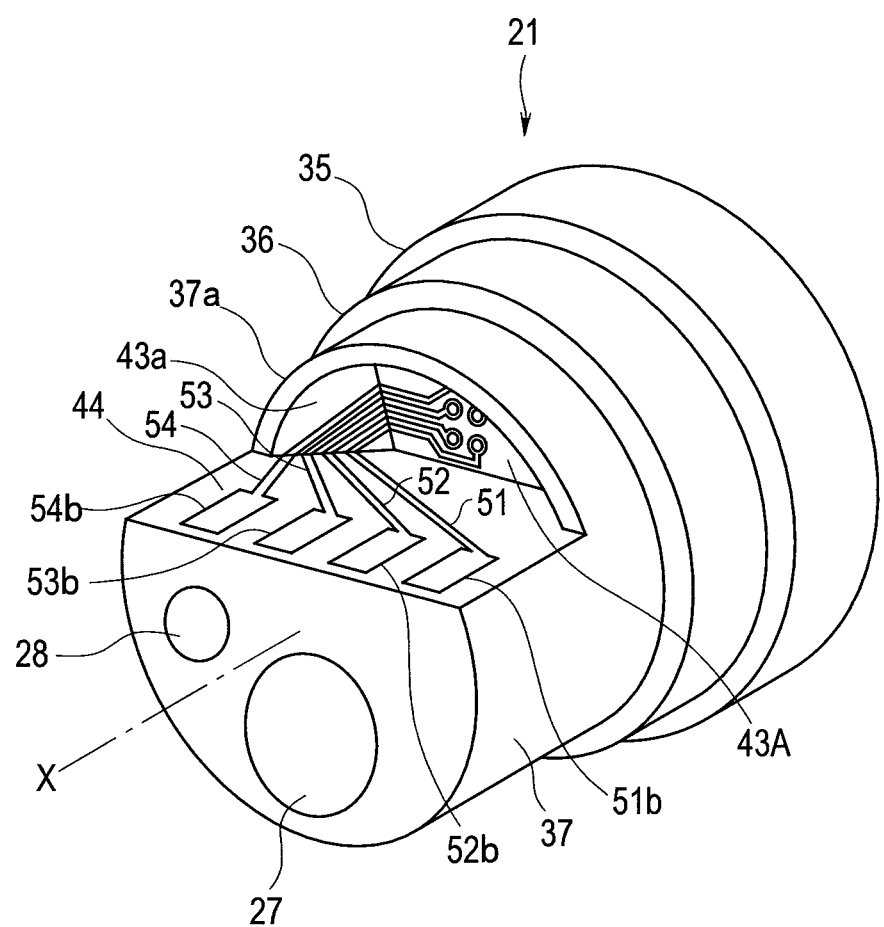
FIG. 40 is a perspective view seen from a proximal end side, and showing a configuration of a distal end barrel member according to a tenth modification of the second embodiment of the present invention.
Figure 41:
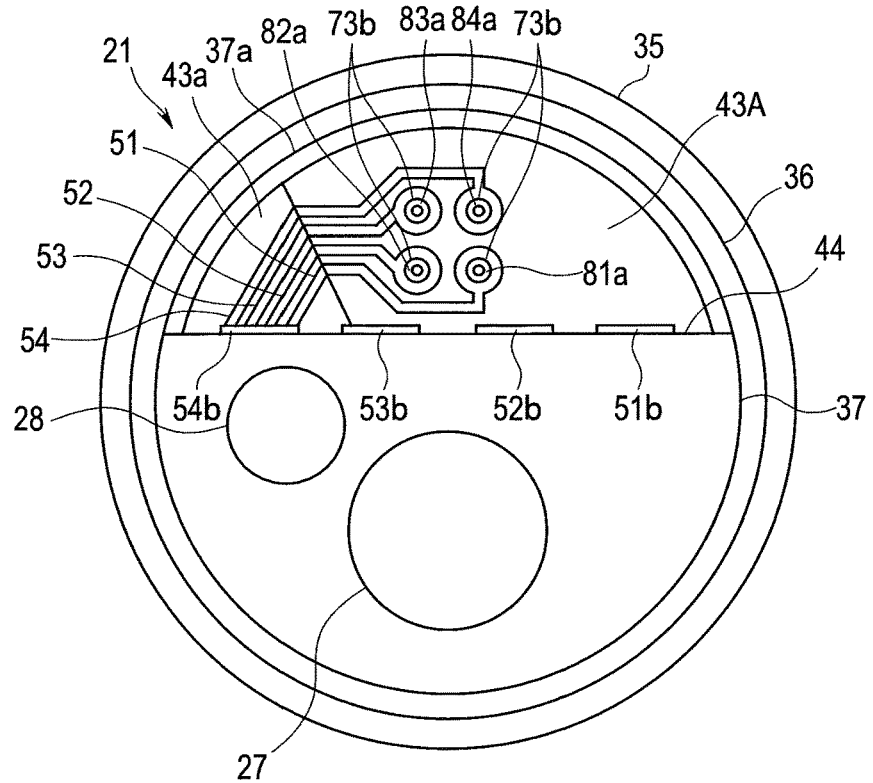
FIG. 41 is a back view showing the configuration of the distal end barrel member in which an inclined surface is formed on one side portion in a rib according to the tenth modification of the second embodiment of the present invention.

As shown in FIG. 40 and FIG. 41, in a distal end barrel member 21, an arc-shaped rib 37a with a predetermined length may be formed along a center axis X in a distal end portion of a second small diameter portion 37 as a fitting portion on which a distal end portion of a bending piece 22A at a distalmost end is fitted. Note that a second wiring formation surface 43A here is not an inclined surface but a vertical surface orthogonal to the center axis X and parallel to a mounting surface 26a of a module accommodation chamber 26.

Thereby, in the distal end barrel member 21, an entire outer periphery of a distal end portion of the second small diameter portion 37 becomes a fitting surface on which the bending piece 22A at the distalmost end is fitted, by the rib 37a, and a fixing force to the bending piece 22A can be increased.

In the distal end barrel member 21, it is possible to easily perform electrical connection of core wires 61a to 64a of cables 61 to 64 to four lands 51b to 54b by soldering or the like without interference of the rib 37a, by forming the four lands 51b to 54b in a region provided to extend to a proximal end side from the rib 37a in a third wiring formation surface 44 that is a cable connection surface.

In the distal end barrel member 21, an inclined surface 43a is formed from the second wiring formation surface 43A to the third wiring formation surface 44, at one side portion inside of the rib 37a, here, on a left side as seen toward a distal end. On the inclined surface 43a, four wiring patterns 51 to 54 are formed from the second wiring formation surface 43A that is a surface orthogonal to the center axis X to the third wiring formation surface 44 that is a surface parallel to the center axis X.

In the distal end barrel member 21, by providing the inclined surface 43a in the rib 37a, it is easier to apply the laser light L to the inclined surface 43a having an angle to the center axis X than in the case of irradiating the laser light L to an inner peripheral surface of the rib 37a that is parallel to the center axis X, and it is possible to easily form conductive paths forming the four wiring patterns 51 to 54 along the inclined surface 43a.

In other words, in the distal end barrel member 21, it is easy to irradiate the laser light L to the second wiring formation surface 43A that is a surface orthogonal to the center axis X and the third wiring formation surface 44 provided to extend to the proximal end side from the rib 37a, but it is difficult to irradiate the laser light to the inner peripheral surface of the rib 37a. Therefore, the inclined surface 43a having an angle to the center axis X is formed in the rib 37a, and irradiation of the laser light L can be made easier.

Figure 42:
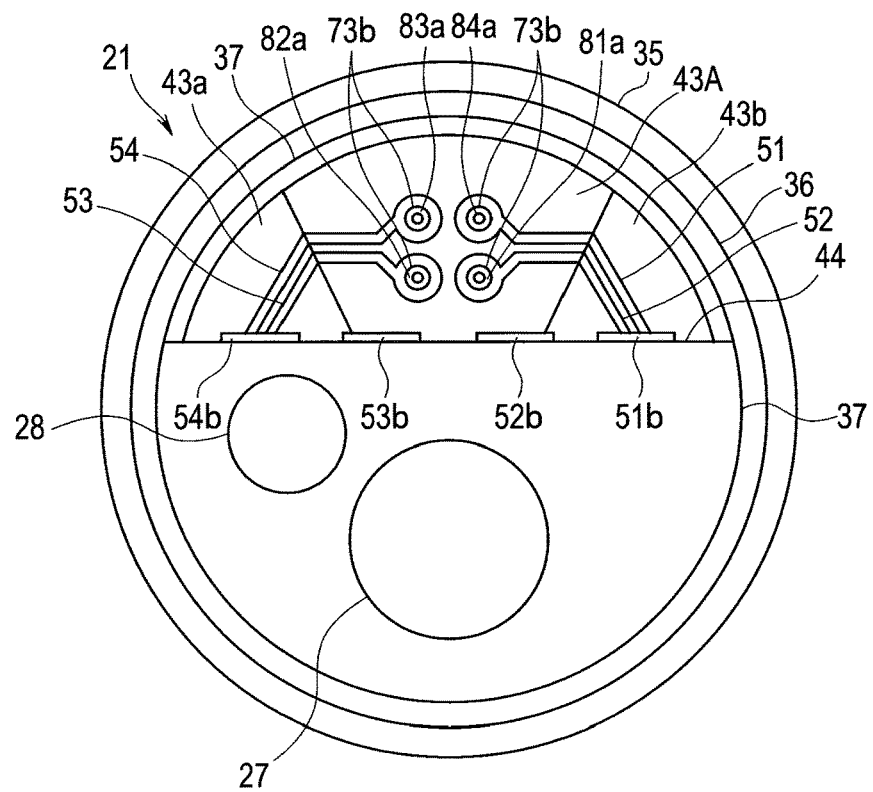
FIG. 42 is a back view showing the configuration of the distal end barrel member in which inclined surfaces are formed on both side portions in the rib according to the tenth modification of the second embodiment of the present invention.

Note that as shown in FIG. 42, inclined surfaces 43a and 43b may be respectively formed on both left and right sides of the distal end barrel member 21, and two wiring patterns 53 and 54 may be formed on an inclined surface 43a side at a left side to a paper surface, whereas two wiring patterns 51 and 52 may be formed on an inclined surface 43b side at a right side to a paper surface.

Eleventh Modification

Figure 43:
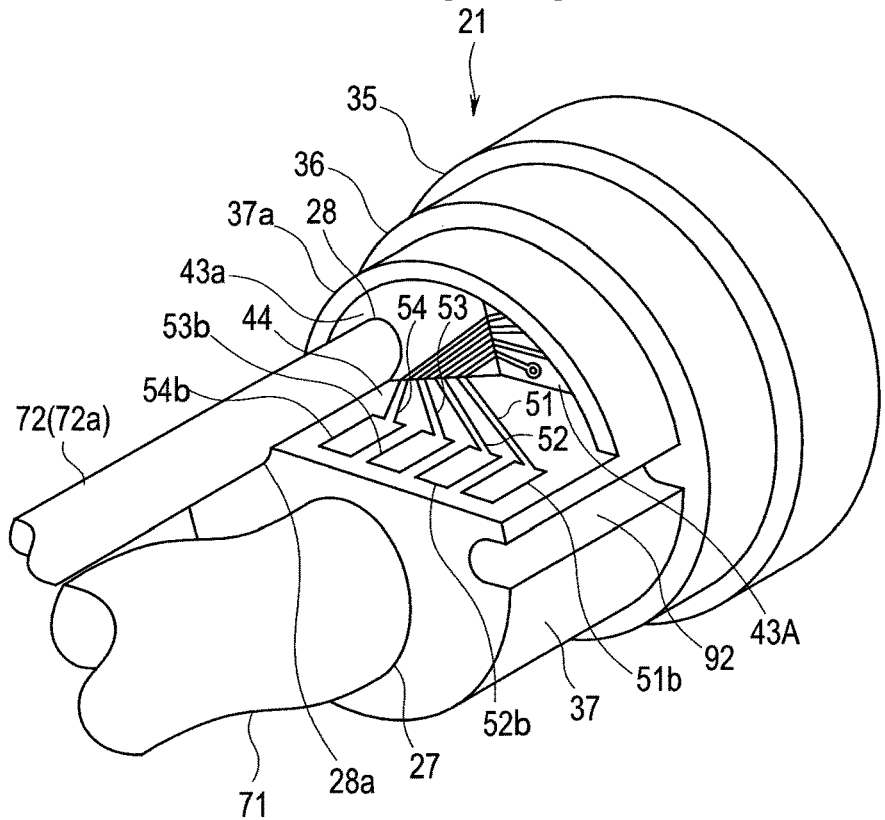
FIG. 43 is a perspective view seen from a proximal end side, and showing a configuration of a distal end barrel member according to an eleventh modification of the second embodiment of the present invention.
Figure 44:
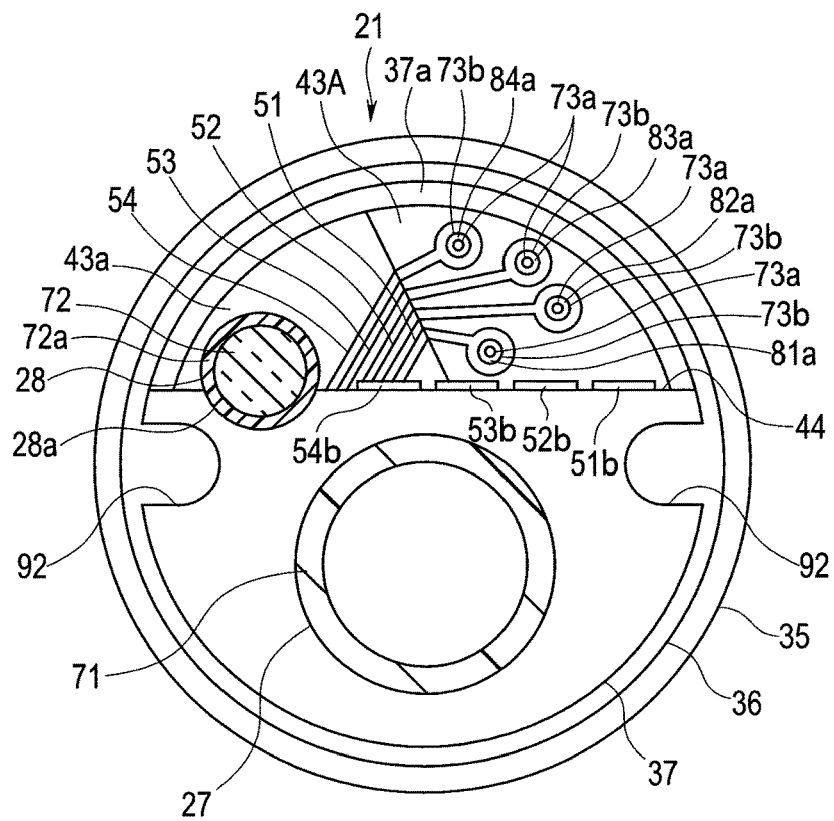
FIG. 44 is a back view showing the configuration of the distal end barrel member according to the eleventh modification of the second embodiment of the present invention.

A distal end barrel member 21 shown in FIG. 43 and FIG. 44 has a configuration in which the ninth modification and the tenth modification are combined. In addition, by providing distal end openings 73a at positions separated from sites where terminals 33a of a camera module 30 are soldered, on a mounting surface 26a of a module accommodation chamber 26, as shown in FIG. 36 of the eighth modification, it is possible to form four through-electrodes 81a to 84a closer to one side part (in an outside diameter direction of the distal end barrel member 21), a right side seen in a proximal end direction here.

Accordingly, on a second wiring formation surface 43A that is a surface orthogonal to a center axis X of the distal end barrel member 21, the four through-electrodes 81a to 84a respectively having proximal end openings 73b are also formed closer to the one side part.

Thereby, the second wiring formation surface 43A can have a predetermined surface area in the one side part, and therefore, an inclined surface 43a in a rib 37a can be formed to have a large surface area from a center side.

In the distal end barrel member 21, it is possible to form a part of an illumination component accommodation chamber 28 that is a hole portion in which a light guide bundle 72 is inserted and disposed, in the inclined surface 43a, by increasing a region of the inclined surface 43a. Note that the illumination component accommodation chamber 28 becomes a recessed portion 28a that is arc-shaped in cross section in a third wiring formation surface 44.

Four lands 51b to 54b are provided side by side on the third wiring formation surface 44 in one side direction (outside diameter direction of the distal end barrel member 21) from the recessed portion 28a so as not to interfere with the light guide bundle 72.

By the configuration like this, it is possible to decrease a diameter in the distal end barrel member 21 because the light guide bundle 72 can be laid out in a position at which the light guide bundle 72 does not interfere with the relief grooves 92 in which wire fixing portions 66a to 66d of a bending piece 22A are disposed. As a result, an outside diameter of a distal end portion 6 of an insertion portion 2 of an endoscope 1 can also be decreased, and the insertion portion 2 can be reduced in diameter.

In each of the embodiments and modifications described above, it is a most efficient production method to subject a surface pattern of the distal end barrel member 21 of an MID structure and terminals of the camera module 30 to a reflow soldering process with the surface pattern of the distal end barrel member 21 facing up and a terminal side of the camera module 30 facing down when the surface pattern of the distal end barrel member 21 of the MID structure and the terminals of the camera module 30 are connected by soldering.

However, in the case of a front-viewing endoscope 1, the terminal side of the camera module 30 is on a proximal end direction side of the endoscope 1, so that a placement surface 26a on which the camera module 30 can be placed during reflow soldering, and the surface pattern can be formed at a position capable of connecting to the terminals of the camera module 30 is formed on the proximal end side of the module accommodation chamber 26.

When the placement surface 26a is located on a back surface of the camera module 30 as above, the distal end barrel member 21 is configured to be able to prevent the outside diameter of the distal end portion 6 of the insertion portion 2 of the endoscope 1 from increasing depending on a connection method of cables for connecting the camera module 30 and various circuits at a hand side and wiring patterns, because wiring patterns can be mainly formed on only a surface of a molded body due to the MID method.

More specifically, it is possible to increase production efficiency of the distal end barrel member 21 of the MID structure by applying reflow soldering by placing the back surface of the camera module 30 on the placement surface 26a of the module accommodation chamber 26 with the back surface of the camera module 30 on a lower side, with a distal end side facing up and a proximal end side facing down, and it becomes easy to widen a connection region and it is possible to make the region wide, by providing a connection region of the cables at a position closer to the center axis X that is an axis than an outside diameter of the distal end barrel member 21. This provides a configuration that enables easy connection of the distal end barrel member 21 and the cables without increasing the outside diameter of the distal end portion 6 of the insertion portion 2 of the endoscope 1.

Further, in recent years, miniaturization of the camera module 30 has also been advanced in response to a request for reduction in diameter of the insertion portion 2 of the endoscope 1. The camera module 30 is loaded on the distal end portion 6 of the insertion portion 2 of the endoscope 1, receives electric power and sends and receives signals to drive, and is electrically connected to an extremal processor to display generated image pickup signals on a monitor.

The above connection generally has a structure via a cable, but since a size and width of the terminals of the camera module 30 are extremely small with miniaturization of the camera module 30, direct connection to the cable becomes difficult. For this reason, if a cable is connected according to the size of the terminal portion of the compact camera module 30, the manufacturing cost increases.

Accordingly, it is possible to increase production efficiency of the distal end barrel member 21 by adopting the MID structure, and applying reflow soldering by placing the camera on the placement surface 26a of the module accommodation chamber 26 with a back surface (undersurface) of the camera on a lower side, with the distal end side facing up and the proximal end side facing down, and connection to the cables becomes easy with the cable connection region secured widely.

Thereby, in the endoscope 1, increase in size of the outside diameter of the distal end portion 6 of the insertion portion 2 can be prevented, and the manufacturing cost can be reduced.

In the MID structure, a wiring pattern can be mainly formed on only a surface of a molded body due to a manufacturing method of the MID structure, and therefore it is necessary to form conductive paths on an outer surface of the distal end barrel member 21 when wiring patterns are drawn to a connection position of the camera module 30 and cables. By providing the through-electrodes 81a to 84a in the conductive paths, it is possible to prevent a circuit length from increasing, and reduce the influence of external noise.

The invention described in the above embodiments and modifications is not limited to the embodiments and modifications, and besides, various changes can be carried out in the range without departing from the gist of the invention in the implementation stage. The above described embodiments and modifications include the inventions in various stages, and various inventions can be extracted by appropriate combinations of a plurality of components that are disclosed.

For example, even if several components are deleted from all the components shown in the embodiments and the modifications, if the problem mentioned can be solved and the effect mentioned is obtained, the configuration from which the components are deleted can be extracted as the invention.

What is claimed is:
1. An endoscope comprising:
an insertion portion configured to be inserted into a subject;
an imager unit comprising an objective optical system, and configured to convert an optical image from the objective optical system into an electric signal; and
a distal end barrel member provided at a distal end portion of the insertion portion, formed of a resin material, and loaded with the imager unit,
the distal end barrel member including:
an imager unit loading region provided at a distal end side, with the imager unit being loaded on the imager unit loading region;
a cable connection surface provided on a proximal end side;
a wall provided to connect an opening of the imager unit loading region and an opening of the cable connection surface to each other;
a contact pattern formed on a wall surface of the imager unit loading region and configured to be electrically connected to an electric contact of the imager unit;

a wiring pattern formed on a front surface of the cable connection surface from the wall and configured to electrically continue to the contact pattern;

a connection pattern formed on the cable connection surface and configured to electrically continue to the wiring pattern, with a core wire of a cable placed in the insertion portion being electrically connected to the connection pattern; and a through-electrode formed on an inner surface of a through-hole that penetrates through the wall so that the imager unit loading region and the cable connection surface communicate with each other, configured to cause the contact pattern and the wiring pattern to electrically continue to each other, and formed at a predetermined angle with respect to a center axis of the distal end barrel member.

2. The endoscope according to claim 1, wherein the through-electrode is formed at a predetermined angle in a direction to be away from the center axis from a distal end side to a proximal end side.

3. The endoscope according to claim 1, wherein the through-electrode is formed at a predetermined angle in a direction to approach the center axis from a distal end side to a proximal end side.

4. The endoscope according to claim 1, wherein
the imager unit loading region is a bottomed hole including an opening at a distal end of the distal end barrel member, with a placement surface on which the imager unit is placed being formed on a proximal end side, and
the placement surface configures a surface on a distal end side of the wall.

5. The endoscope according to claim 4, wherein the imager unit loading region also includes an opening in one direction in an outer periphery of the distal end barrel member, and is in a recessed portion shape similar to an outer shape of the imager unit.

6. The endoscope according to claim 1, wherein in the distal end barrel member, a fitting portion that is fitted to a distal end of the insertion portion is formed at a proximal end portion.

7. The endoscope according to claim 6, wherein
the fitting portion is in a substantially cylindrical shape, and
a connection portion of the connection pattern and the core wire of the cable is disposed on a proximal end side from the fitting portion.

8. The endoscope according to claim 7, further comprising a bending portion provided connectively at a proximal end of the distal end portion,
wherein a connection portion of the connection pattern in plurality and the core wire of the cable is formed between a proximal end of the wall and a distal end of the bending portion.

9. The endoscope according to claim 7,
wherein a connection portion of the connection pattern in plurality and the core wire of the cable is provided to protrude in an inside diameter direction in the bending portion, is located at a distal end side from a wire fixing portion configured to fix a distal end of a bending operation wire configured to operate to bend the bending portion, and is superimposed on an inside of a projection along the center axis.

10. The endoscope according to claim 1, wherein the cable connection surface is formed between an outer peripheral portion of the wall and the center axis.

11. The endoscope according to claim 10, wherein the cable connection surface is a flat surface parallel along the center axis.

12. A distal end barrel member of an endoscope including an insertion portion configured to be inserted into a subject,
the distal end barrel member being provided at a distal end portion of the insertion portion, and comprising:
an imager unit loading region on which an imager unit configured to convert an optical image from an objective optical system into an electric signal is loaded;
a cable connection surface provided on a proximal end side;
a wall provided to connect an opening of the imager unit loading region and an opening of the cable connection surface to each other;
a contact pattern formed on a wall surface of the imager unit loading region and configured to be electrically connected to an electric contact of the imager unit;
a wiring pattern formed on a front surface of the cable connection surface from the wall and configured to electrically continue to the contact pattern;
a connection pattern formed on the cable connection surface and configured to electrically continue to the wiring pattern, with a core wire of a cable placed in the insertion portion being electrically connected to the connection pattern; and
a through-electrode formed on an inner surface of a through-hole that penetrates through the wall so as to connect the opening of the imager unit loading region and the opening of the cable connection surface to each other, configured to cause the contact pattern and the wiring pattern to electrically continue to each other, and formed at a predetermined angle with respect to a center axis of the distal end barrel member.

13. An insertion portion of an endoscope configured to be inserted into a subject,
the insertion portion being provided with a distal end barrel member at a distal end,
the distal end barrel member comprising:
an imager unit loading region on which an imager unit configured to convert an optical image from an objective optical system into an electric signal is loaded;
a cable connection surface provided on a proximal end side;
a wall provided to connect an opening of the imager unit loading region and an opening of the cable connection surface to each other;
a contact pattern formed on a wall surface of the imager unit loading region and configured to be electrically connected to an electric contact of the imager unit;
a wiring pattern formed on a front surface of the cable connection surface from the wall and configured to electrically continue to the contact pattern;
a connection pattern formed on the cable connection surface, and configured to electrically continue to the wiring pattern, with a core wire of a cable placed in the insertion portion being electrically connected to the connection pattern; and
a through-electrode formed on an inner surface of a through-hole that penetrates through the wall so as to connect the opening of the imager unit loading region and the opening of the cable connection surface to each other, configured to cause the contact pattern and the wiring pattern to electrically continue to each other, and formed at a predetermined angle with respect to a center axis of the distal end barrel member.

\* \* \* \* \*